(12) United States Patent
Hines et al.

(10) Patent No.: US 11,893,534 B2
(45) Date of Patent: Feb. 6, 2024

(54) SYSTEM FOR INVENTORY MANAGEMENT

(71) Applicant: HME360 BI, LLC, New Orleans, LA (US)

(72) Inventors: Bryan D. Hines, New Orleans, LA (US); John Skoro, Plano, TX (US)

(73) Assignee: HME360 BI, LLC, New Orleans, LA (US)

( * ) Notice: Subject to any disclaimer, the term of this patent is extended or adjusted under 35 U.S.C. 154(b) by 327 days.

(21) Appl. No.: 15/929,686

(22) Filed: May 15, 2020

(65) Prior Publication Data

US 2020/0364660 A1  Nov. 19, 2020

Related U.S. Application Data

(60) Provisional application No. 62/848,338, filed on May 15, 2019.

(51) Int. Cl.
| | | |
|---|---|---|
| *G06Q 10/0875* | (2023.01) | |
| *G06Q 40/08* | (2012.01) | |
| *G08B 13/24* | (2006.01) | |
| *G16H 30/20* | (2018.01) | |
| *G16H 40/40* | (2018.01) | |

(52) U.S. Cl.
CPC ......... *G06Q 10/0875* (2013.01); *G06Q 40/08* (2013.01); *G08B 13/2454* (2013.01); *G16H 30/20* (2018.01); *G16H 40/40* (2018.01)

(58) Field of Classification Search
None
See application file for complete search history.

(56) References Cited

U.S. PATENT DOCUMENTS

| | | | |
|---|---|---|---|
| 8,818,824 B2 | 8/2014 | DeBusk et al. | |
| 9,990,466 B2 | 6/2018 | DeBusk et al. | |
| 10,152,688 B2 | 12/2018 | DeBusk et al. | |
| 10,445,593 B1 * | 10/2019 | Mathiesen | G06V 20/53 |

(Continued)

FOREIGN PATENT DOCUMENTS

WO   2013/032642 A1   3/2013

OTHER PUBLICATIONS

European Patent Office, "Supplementary European Search report and Search Opinion," issued in connection with European Patent Application No. 20805743.0 dated Dec. 8, 2022 13 pages.

(Continued)

*Primary Examiner* — Devin C Hein
(74) *Attorney, Agent, or Firm* — Holland & Hart LLP

(57) ABSTRACT

The present disclosure includes an inventory fulfillment system for managing information regarding pertaining to the inventory supply chain logistics and automation of medical items dispensed in conjunction with medical treatment of a patient at a medical facility, wherein the medical items are stored in a physical inventory space in the medical facility, wherein the medical items have radiofrequency tags attached thereto is disclosed herein. In some implementations, the inventory fulfillment system receives, dispenses, and manages, medical items that are provided by a multiplicity of suppliers, collects patients' payments. In some implementations, the inventory fulfillment system also includes assigning items to patients, updating inventory applications, insurance eligibility, patient estimation, and patient payment.

18 Claims, 12 Drawing Sheets

(56) References Cited

U.S. PATENT DOCUMENTS

| | | | | |
|---|---|---|---|---|
| 2009/0066515 | A1* | 3/2009 | Kangas | G08B 13/248 |
| | | | | 340/572.1 |
| 2012/0253852 | A1 | 10/2012 | Pourfallah et al. | |
| 2013/0039543 | A1* | 2/2013 | Fuhr | G08B 27/00 |
| | | | | 382/103 |
| 2014/0372143 | A1* | 12/2014 | Kennedy | G06Q 10/10 |
| | | | | 705/2 |
| 2016/0110780 | A1* | 4/2016 | DeBusk | G16H 10/60 |
| | | | | 705/3 |
| 2018/0240066 | A1* | 8/2018 | Streebin | G06Q 10/0838 |
| 2018/0278897 | A1* | 9/2018 | Seaman | H04N 7/181 |

OTHER PUBLICATIONS

International Search Report and Written Opinion of the International Searching Authority, issued in connection with Int'l Appl. No. PCT/US2020/070055, dated Aug. 18, 2020 (6 pages).

* cited by examiner

SYSTEM FOR INVENTORY MANAGEMENT

CROSS REFERENCE

The present Application for Patent claims priority to U.S. Provisional Patent Application No. 62/848,338 by Hines et al., entitled "SYSTEM FOR MEDICAL ITEM DISPENSING, BILLING, PATIENT COLLECTIONS AND INVENTORY MANAGEMENT," filed May 15, 2019, assigned to the assignee hereof, and which is expressly incorporated by reference in its entirety herein.

FIELD OF TECHNOLOGY

This disclosure relates to an inventory fulfillment system of supply items in a facility.

BACKGROUND

Home medical equipment (HME) is a category of devices used for patients whose care is being managed from a home or other private facility managed by a nonprofessional caregiver or family member. It is often referred to as durable" medical equipment (DME) as it is intended to withstand repeated use by non-professionals or the patient and is appropriate for use in the home.

DME, Prosthetics, Orthotics and Supplies (DMEPOS) as defined by the Department of Health and Human Services and its Center for Medicare Services (CMS) is a class of medical devices, products and supplies that can be reimbursable under Part B of the U.S. Medicare health care program. In general, this category of products includes items provided to patients who receive outpatient treatment for certain health problems that do not require inpatient admission to a hospital or other healthcare institution. DMEPOS items may be provided or prescribed to help alleviate, treat or assist in recovery from the condition that prompted the outpatient treatment of the patient. Such outpatient treatment can occur in any number of settings, such as a hospital emergency department, a clinic, or a physician's or therapist's office.

In general, the costs of DMEPOS items are reimbursable or payable separately from the healthcare professional's fee for treatment of the patient. DMEPOS items may be reimbursable or payable in both Medicare and Medicaid programs and through private health insurers. Traditionally, most DMEPOS items have been prescribed by the treating professional and those prescriptions filled by DME shops, Orthotics/Prosthetics shops, pharmacies with DME services, etc. However, as a convenience to patients many healthcare providers wanted to dispense DMEPOS items at the time of treatment of the patient in order to facilitate patient convenience and continuity of care.

Healthcare providers began dispensing DMEPOS items as an adjunct service to their medical practice. Healthcare providers have been supplying the patient with DMEPOS products that the healthcare provider has evaluated and knows to be appropriate for the patient's particular diagnosis and indications. It is a significant advantage for the patient that the healthcare provider provides the DMEPOS item at the time of initial diagnosis and treatment of the patient. The healthcare provider properly fits the item to the patient and instructs the patient on the proper use of the item. For the patient, this minimizes the hassle of having to go to other locations to complete the diagnosis and treatment, and generally results in better continuity of care.

Since DMEPOS items may be reimbursable or payable under a different billing and reimbursement system than professional healthcare services, it can be difficult for healthcare professionals to provide the dispensing of these items as an adjunct service to their patients. The specialty shops that have traditionally dispensed these items have developed the business processes necessary to properly stock the products, manage the inventory, properly associate prescriptions for DMEPOS items with appropriate coding under the CMS coding system, generate the regulatory paperwork for delivery of the item to the patient and generate the necessary forms for submission to the reimbursement agency such as Medicare, Medicaid, or private insurance.

Further, hospitals, outpatient facilities, and other healthcare providers have been stocking DMEPOS products onsite and interfacing with DMEPOS suppliers to track the dispensing of DMEPOS products to their patients. The DMEPOS products have been stored in dedicated space, such as a medical supply closet, at the healthcare providers' locations.

Each DMEPOS supplier tracks its own inventory and handles the patient billing. Since each DMEPOS supplier has developed their own inventory tracking system, healthcare providers are often forced to have multiple inventory storage spaces within their facility to house multiple DMEPOS manufacturer's products. The healthcare provider may be required to make space onsite for a closet for each DMEPOS supplier that it would like to dispense to its patients. Many healthcare providers simply do not have the space to accommodate multiple closets, specifically for isolating and securing products by DMEPOS vendor or supplier. Setting aside space in the facility, maintaining inventory, ensuring proper authorization in the storage spaces, assigning the DMEPOS products to the patient, and billing and patient collections associated with the DMEPOS products are real challenges for healthcare providers.

Other inventory solutions may not be able to handle the communication between multiple DMEPOS suppliers, multiple medical facilities, and billing management of any medical item from eligibility to payment regardless of which DMEPOS supplier has supplied that medical item.

Healthcare providers would like to eliminate the need for multiple closets that store and secure DMEPOS products from multiple vendors and suppliers. Healthcare providers would like to have a storage space and solution that tracks inventory from multiple DMEPOS suppliers, and that handles the dispensing, eligibility, billing, and payment of any and all DMEPOS to the patients.

Lastly, DMEPOS vendors and suppliers would like to have a single point of visibility and management from their respective warehouse distribution centers with drill down visibility into any and all their DMEPOS supply closets.

SUMMARY

The disclosed technology includes an inventory fulfillment system that can be implemented in a single storage space (e.g., one medical supply closet) and solution that tracks and stores inventory from multiple suppliers, and that handles the dispensing, eligibility, billing, and payment of inventory items to the patients. In some implementations, the disclosed technology includes RFID automated inventory management, Electronic Data Interchange reordering and e-delivery generation, e-Prescribing and e-delivery generation, billing system integration, processing for co-pay capture, cloud-based and universal closet visibility, open/share environment capabilities, and expanded product formulary.

Specifically, in some implementations, the disclosed inventory fulfillment system and methods are directed to managing information, claim processing, and payment collection regarding medical items dispensed in conjunction with medical treatment of a patient at a medical facility, wherein the medical items are stored in a physical inventory space in the medical facility, and wherein the medical items have RFID tags attached thereto that identify the medical items to which the RFID tags are attached.

The inventory fulfillment system may include one or more computers associated with the medical facility, an inventory space within the medical facility storing the medical items, one or more computers associated with an inventory management service supplier, one or more RFID sensors for sensing the presence of RFID tags attached to medical items in the inventory space, in communication with the one or more computers associated with the inventory management service supplier via a communication network, the inventory sensors for sensing removal of one or more medical items from the inventory space, for generating item usage information indicative of an identity and quantity of the one or more medical items removed, and for identifying a user of the inventory space; one or more software applications executed on the one or more computers associated with an inventory management service supplier, the one or more software applications including computer-executable instructions which, when executed: record the removal of the one or more medical items removed in an inventory application; upon the sensors sensing removal of the one or more medical items, associate the item usage information of the medical items removed with the user that removed the medical items; and generate a record to be sent to the one or more computers of the medical facility over the communication network that includes assignment of medical items removed to the identified user.

One or more software applications executed on the one or more computers of the medical facility includes computer-executable instructions which, when executed: access the record sent from the inventory management service supplier that includes assignment of medical items removed to the identified user, access a patient database associated with the one or more computers of the medical facility, the patient database storing information associated with the patients of the medical facility, and generate one or more records associating the one or more medical items removed with one or more patients.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the claimed subject matter will be apparent from the following more particular written Detailed Description of various implementations as further illustrated in the accompanying drawings and defined in the appended claims.

These and various other features and advantages will be apparent from a reading of the following Detailed Description.

DETAILED DESCRIPTION

Figure 1:
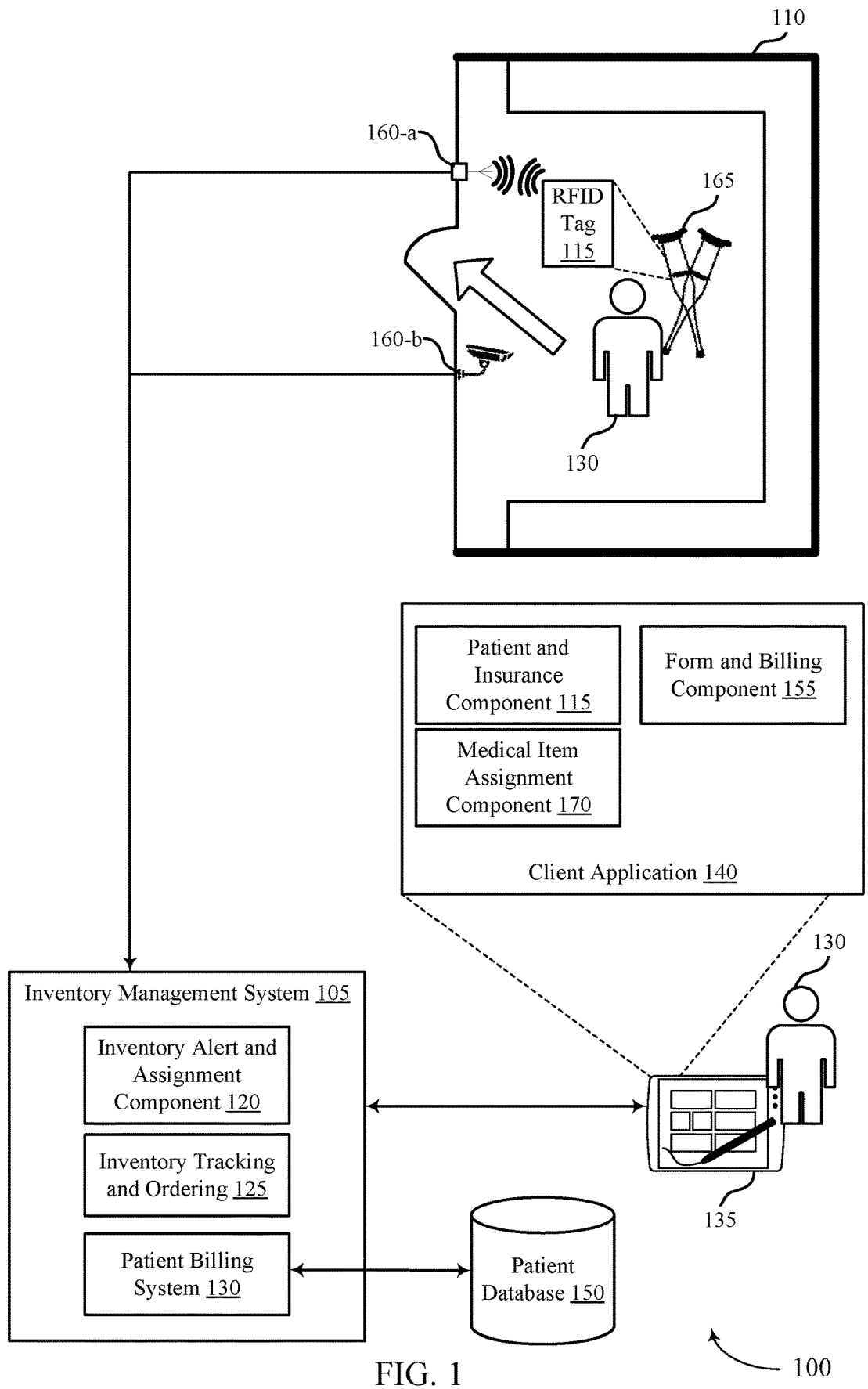
FIG. 1 is a block diagram that illustrates an example environment for implementing an inventory fulfillment system in accordance with aspects of the present disclosure.

Treatment of a patient at a treatment facility, including a hospital emergency department, a physician's office, a clinic, and a therapy office, generally follows a series of steps, including the patient arriving at a treatment facility with a medical condition and ends with the patient being discharged or leaving the treatment facility. Patient intake, in which information concerning the patient is recorded and a patient record/chart (or face sheet) is created as an output. Patient intake may include collecting of basic demographic and medical information about the patient, as well as payment responsibility information, such as insurance information (either private insurance or information regarding participation in a government program such as Medicare/Medicaid). This information is recorded in the patient record/chart, which is may be created in electronic form in a pre-existing information system resident in the treatment facility.

Following patient intake is the examination of the patient. The appropriate healthcare provider examines the patient, takes a patient history, and reviews the symptoms. The examination may also include other diagnostic activities such as lab work and imaging that assist the provider in making an accurate diagnosis. Examination information may be recorded into the patient record/chart. The healthcare provider then makes a diagnosis of the patient and the diagnostic information may also be entered into the patient record/chart.

After diagnosis and entering the diagnostic information in the patient record/chart, the next step may be treatment of the patient. In the context of this disclosure, treatment of the patient may include the healthcare provider prescribing or providing medical equipment (e.g., a Durable Medical Equipment (DME), Prosthetics, Orthotics and Supplies (DMEPOS) item, such as an orthotic,) to facilitate treatment of the diagnosed condition. Information regarding the treatment, including prescription information (e.g., a DMEPOS prescription), is entered into the patient record/chart, and this information is entered in the patient's Electronic Medical Records (EMR).

Traditionally, once the patient is ready to be discharged or released, the information entered into the patient record/chart is used to supply information to create a medical compliant bill reflecting all of the billable services provided in the process. This information is then uploaded to the appropriate billing software for submittal to payer.

In the disclosed inventory fulfillment system, or inventory management system, the medical facility may not communicate to the individual supplier (e.g., DMEPOS supplier). Instead, the medical facility may communicate to an inventory management service supplier. The customer computer network and an inventory management service supplier computer network may communicate a communication network. The disclosed inventory management system manages information regarding medical items dispensed in conjunction with medical treatment of the patient at the medical facility, wherein the medical items are stored in a physical inventory space in the medical facility, wherein the medical items have radiofrequency (RFID) tags attached thereto.

In some implementations, the inventory management system dispenses, manages, collects patients' payments, and bills for medical items (e.g., home medical equipment (HME) medical items) that are provided by suppliers (e.g., HME suppliers). The inventory management system includes assigning items received from a supplier to patients, updating inventory applications, insurance eligibility, patient estimation, billing (e.g., insurance claims billing), and patient payment.

The disclosed technology offers the capability of prompt inventory deliveries with just in time processing and status acknowledgments (e.g., Electronic Data Interchange (EDI) status acknowledgments). A facility central supply is provided with at least one supply closet at a medical facility with tablet (or other device) check out providing higher patient experience (e.g., no waiting for DME deliveries) and faster patient discharges. The disclosed technology may also provide for EDI reorders. The disclosed technology automatically acknowledges receipt of goods, rebalances inventory level as inventory is moved, discharges DME to the patient and reorders on PAR thresholds, and return of medical items.

While specific examples in the present disclosure are directed towards medical equipment in a medical facility, other applications are contemplated. For example, the disclosed system may be used for inventory management in a variety of industries. For example, aspects of the present disclosure are described with respect to medical items and a medical facility, but the described inventory space may be implemented in other industries, as well as in various aspects of a supply chain including warehouses and the like.

As the term is used herein, "clinician" generally refers to a clinician, physician, nurse, healthcare assistant, healthcare provider, dispenser, or otherwise employee who has access to the medical equipment, dispenses medical items, or otherwise utilizes the inventory management or fulfillment system. In some implementations, where the inventory management system is utilized in another type of facility or warehouse distribution system, the clinician may be any individual, operator, user, or administrator having access to equipment in the inventory management or fulfillment system.

As the term is used herein, "medical items" refers to any item, product, supplies, or goods managed in the inventory fulfillment system. For purposes of illustration, the examples include medical items (e.g., DME, DMEPOS, HME) in a medical facility setting. However, in some implementations, the items may be other medical items, non-medical items, or items used in a non-medical setting, and referred to as "inventory items."

As the term is used herein, "customer" generally refers to a medical facility where medical diagnostic and treatment procedures are performed, such as a hospital, outpatient surgical center, physician's office, clinic, or therapy office. The term "customer" may also refer to any consumer of products/supplies that are inventoried and managed using the system described herein. Accordingly, one or more of the components of the customer computer network may be located within a hospital, clinic, doctor's office, or other medical facility. In some implementations, a customer may be a company utilizing the disclosed inventory management system in a warehouse environment.

As the term is used herein, "facility" generally refers to the location, building, store, room, warehouse, clinic, office, hospital, pharmacy, or otherwise dispensing environment or place that houses the medical or inventory items in the inventory fulfillment system. For purposes of illustration, the facility is described herein as a medical facility.

As the term is used herein, "inventory management service supplier" generally refers to an entity that supports the inventory management system described herein and may be a supplier of medical or other inventory items. In some examples, an inventory management service supplier may support a facility, such as a medical facility, warehouse facility, or other facility that holds inventory items, in inventory management.

The medical facility and an inventory management service supplier may communicate via internet, intranet, and the like. The inventory management service supplier communicates with the other entities of the disclosed inventory management system, such as medical item suppliers, home medical equipment (HME) suppliers, an insurance eligibility application, a billing management application, facility computing systems (e.g., patient databases), via cloud computing systems or other types of communications systems. For example, communications systems may support automated on-demand service to multiple entities via an application programming interface (API) over a network to a shared pool of configurable computing devices used to implement requests from the external entities for computing resources, such as data storage, application execution, and database management computing resources.

As the term is used herein, an "inventory space," "closet," or "storage container" may be a secured, limited access inventory room or supply room in a facility. Alternatively, an inventory space may be a storage structure, such as cabinet, box, cage, shelf or shelving unit, or other enclosure or structure. In some implementations, multiple inventory spaces may be provided in a single room. For example, there may be one secured cabinet containing medical items and another secured cabinet in the same supply room containing surgical implant items. In some implementations, the inventory space may be an unsecured space into which anyone may enter or gain access.

The medical items (e.g., DMEPOS items) may be items that have been obtained from multiple medical item suppliers and multiple medical item manufacturers. The inventory management system provided herein is an inventory solution that dispenses, tracks, and bills for all medical items regardless of supplier or manufacture. As a result, the hospital or medical facility does not have to sort medical items into multiple storage locations.

As described herein, an inventory space may be an example of a secured or closed space or an open space. A secured/closed space is an example of an inventory space that may require the utilization of authorization before the space is accessed. Authorizations may include swiping a key card, entering a key code, a biometric access technique, or the like. An open space is an example of an inventory space in which a user that has access to the facility housing the inventory space may access. That is, if the user has access to the facility, then the user may access the inventory space. An open space (as well as a closed space) may implement RFID sensors, cameras, and the like to track the removal and arrival of inventory as well as the user(s) that perform such actions. For example, in an open space, RFID sensors may identify a user based on the detection of an RFID tag on the user's badge. Further, cameras may track the removal of items by authorized and unauthorized users.

FIG. 1 illustrates an environment 100 for implementing an inventory fulfillment or management system 105 as described herein. The inventory management system 105 may be supported by inventory management services suppliers (shown and described as inventory management services suppliers 405 and 605) as described with respect to FIGS. 4A, 4B, 6A, and 6B. The environment 100 includes the inventory management system 105, and an inventory space 110. The inventory management system 105 may be hosted by a computing system of a medical facility and/or in a separate computing system managed by the inventory management supplier. The inventory space 110 may be an example of one or more inventory spaces of a medical facility 410 or 610 as described with respect to FIGS. 4A, 4B, 6A and 6B. The inventory management system 105 may be configured to communicate (e.g., using wired and/or wireless communication facilities) with one or more sensors 160 that are implemented in the inventory space 110. FIG. 1 is described with respect to inventory space 110 in a medical facility, but it should be understood that various aspects are applicable to other facilities, such as warehouses.

The inventory space 110 may hold a plurality of items, such as medical item 165. These medical items may be prescribed/assigned to patients by an authorized user, such as a clinician or physician. In some examples, the inventory space 110 is a closed and secured space that may be accessed upon authorization (e.g., using a key card, number entry, etc.). In other cases, the inventory space 110 is an open space, in which a person with access to the facility may access the inventory space 110. Aspects of the disclosure described herein may be applicable to both open and closed spaces. For example, the RFID sensors and or cameras may be used to determine the identity of a user removing items from the inventory space 110, as will be described in further detail below. Each of the medical items within the inventory space may be configured with an RFID tag, or other electronic identifying facility, as described herein. As an example, medical item 165 may be implemented with an RFID tag 115. The inventory management system 105 may maintain an association between identifiers associated with the RFID tag (e.g., an electronic product code) and the item. Thus, when an item is detected as being removed/returned, the system may be able to identify the removed/returned item.

A user 130 may enter the inventory space 110 (e.g., whether open or closed) and retrieve a medical item 165 and remove the medical item 165 from the inventory space 110.

The sensor 160-a, which may be an example of an RFID reader, may identify the RFID tag 115 as being removed from the inventory space 110. The sensor 160-a may make such a determination based on not being able to detect the RFID tag 115 within the field of detection or based on the RFID passing through an area that indicates removal. Further, the sensor 160-b, which may be an example of a camera (e.g., a security camera) may capture an image of the user 130. The image may be captured or stored upon detection of removal of the medical item 165.

The inventory management system 105 may receive an indication of removal of the medical item 165 from the sensors 160. The indication may be received over various communication protocols such as through cellular communication, data communication, internet communication, etc. In some examples, the indication may be generated and transmitted by a computing system supported by the medical facility and/or the inventory management supplier. The indication of removal may include an indication of an identity of the user 130 that removed the item. The identity may be based on the authorized access (e.g., using a key card), an identity recognized by the RFID system (e.g., an RFID tag on the user's badge), an identify recognized by the camera (e.g., sensor 160-b) and associated systems (e.g., an image recognition system), etc.

An inventory alert and assignment component 120 of the inventory management system 105 may support inventory removal and unassigned alerts, as well as assignment of removed items. In one example scenario, the medical item 165 (e.g., a pair of crutches) is detected as being removed, but the user is unidentified (e.g., an unknown identity). In such cases, the inventory alert and assignment component 120 may generate and transmit alerts to various parties, including an administrator of the medical facility or the inventory space 110, the inventory management supplier, etc. In some examples, the alert may be transmitted to a client application that may be executed on devices of employees of the medical facility, such as device 135. For example, a notification received regarding a lost product may be: "COMMODE,3-IN-1,STEEL/00 01 00 00 03 EC 00 00 00 00 00 00 has been moved to the Lost Products table and billed to Medical Facility A." Or in another example, a notification received regarding a product left the closet with an unassigned user may be: "Product COMMODE,3-IN-1, STEEL/00 01 00 00 03 EC 00 00 00 00 00 01 left closet Medical Facility A Closet 1 and was not assigned to a clinician."

The alert may include a link (e.g., a uniform resource locator (URL)) or other indication to the image captured by the sensor 160-b such that the user may be identified. The image may be still image, a video, etc. of the user 130 that removed the medical item 165. Accordingly, the parties may take appropriate action to retrieve the medical item 165 and/or correct assignment to an authorized user. Thus, using these alert processes, the medical facility and/or the inventory management supplier may reduce costs associated with lost medical items. In some cases, if the unauthorized removal of the item 165 is not corrected within a predetermined amount of time (e.g., twenty-four hours), then the inventory management system 105 may automatically generate and transmit a bill to the medical facility for the cost of the removed medical item 165.

Further, various inventory correction processes may be automatically activated, such as automatic ordering of a replacement item. In these and other cases, the inventory alert and assignment component 120 generates a record of the item removal, and the record may include an identity of the user (e.g., an unknown identity, in the above example). Further, the image may be stored in association with the removal record.

In another scenario, the user 130 is an authorized user (e.g., a clinician), as detected by the sensor 160-b (e.g., camera) or other authentication processes (RFID reader, access card). In such cases, the inventory management system 105 may receive the indication of the item removal and generate the removal record. The record may specify item usage information that may be associated with the user 130. That is, the items that are removed may be assigned to the user 130. Further, an image of the user 130 may be stored in association with the removal record. The inventory alert and assignment component 120 may transmit (e.g., an API request) an indication of the record (e.g., assignment) specifying the item usage information and the identity of the user to the client application 140.

The client application 140 may be an example of a downloadable application or a web-application (e.g., accessed via a web browser) that may access various services supported by the inventory management system 105. For example, the client application 140 may be an example of the home page that is accessible via the hospital clinician as described with respect to FIG. 5. The client application 140 may configured for various levels of access as described with respect to FIG. 5, including hospital administrator access, Provider operator access, etc.

The client application 140 may be accessed by the user 130 (e.g., a clinician) to perform various services, such as assignment of a removed item to a patient, billing, payment, etc., as described herein. For example, as the client application 140 has received item removal information for the user 130, the user may access the client application 140 to assign one or more of the removed items to a patient using medical item assignment component 170. Thus, the user 130 may identify/retrieve patient information or input patient information using the application 140 (e.g., via a patient and insurance component 145). In some cases, the patient information is retrieved using a patient database 150 hosted by the medical facility or associated parties, which is accessed by the inventory management system 105. Thus, such information may be accessed via the patient and insurance component 145 and the inventory management system 105. Whether the information is inserted or retrieved, the user 130 may assign the item using the medical item assignment component 170. The patient and insurance component 145 may be used to perform an insurance eligibility check of the assigned item in real-time or near real-time. Thus, this service may activate an API request (or other communications process) to the insurance provider or associated parties (e.g., an insurance aggregation service) to determine insurance eligibility, copay information, etc. to determine a bill estimation. Thus, using the user device 135, the user 130 may determine eligibility and copay information while in contact with the patient.

Form and billing component of the client application 140 may request and receive forms generated by the inventory management system 105. Thus, the inventory management system 105 may receive the patient and medical equipment assignment information, generate the appropriate forms based on the insurance information and patient information, and transmit the forms to the device 135 for display and acceptance (e.g., click through or signature). In some cases, the form and billing component 155 may access patient billing system 130, which may access a payment gateway 430 of FIG. 4. The billing system 130 may support receipt of payment via the form and billing component 155 of the client application 140. That is, the form and billing component 155 may leverage a third party payment system (e.g., payment gateway 430) to accept payment at the device 135 (e.g., using a credit card). Further, the form and billing component 155, in association with the patient billing system 130, may transmit the appropriate receipts and forms for billing the insurance, as described herein.

Thus, because the removed items may be assigned to the clinician (e.g., authorized user) that removed the items, the clinician may use the client application 140 to assign the items to a patient, check insurance eligibility, accept payment, etc. using the user device 135. The inventory management system 105 supports the client application 140 in management of various communications between multiple parties, providing an efficient and user friendly medical device management and prescribing system.

When a medical item is removed by the user 130 and from the inventory space 110, the inventory tracking and ordering component 125 of the inventory management system 105 may monitor a duration of item removal. In some examples, this includes activating a timer associated with each removed item. If the duration associated with an item exceeds a threshold (e.g., the timer expires), then the inventory alert and assignment component 120 may trigger an unassigned item alert. Thus, various parties may be alerted that an item has been removed by an authorized party (e.g., a clinician) but has not been assigned to a patient and/or returned to the inventory space 110 for an extended period. Thus, the parties may take appropriate action to locate the item and/or the clinician. This process may reduce the probability of items being lost or unaccounted for, reducing costs for the various parties as described herein. As was described with the unauthorized item, if an item is unassigned for some predetermined period, the inventory management system 105 may automatically generate and transmit a bill for the unassigned item and take appropriate inventory actions (e.g., ordering new items).

The inventory tracking and ordering component 125 may also take various inventory actions associated with the inventory space 110, the medical facility, and other inventory spaces and facilities. When an item is removed by user 130, the inventory associated with the inventory space 110 and/or the medical facility may be temporarily reduced for the removed item(s). When the item is assigned to the patient using the client application 140, the inventory may be permanently reduced (at least until the item or a replacement item is moved into the inventory space 110). The inventory tracking and ordering component 125 may monitor the inventory for each item, and when an item reaches a threshold level, the inventory tracking and ordering component 125 may automatically generate and transmit order forms for the item. The items may be automatically ordered from the appropriate suppliers (e.g., supplier 620 of FIGS. 6A and 6B).

In some examples, the inventory tracking and ordering component 125 may consider minimum freight levels for a supplier before placing an order. If the freight level is not satisfied, then the component 125 may trigger an alert to the appropriate parties. In such cases, authorized users may identify other medical items that are not at a threshold that may be ordered to satisfy freight requirements. These systems may also consider an order deadline associated with the supplier. Thus, if the deadline is approaching, then the component 125 may generate the alert. Further, the component 125 may consider minimum freight associated with multiple medical items in determine whether to place the order and/or to trigger the alert. That is, the quantity and costs of multiple medical items may be aggregated to determine the freight requirements. Further, when a medical item is returned to the inventory space 110, the sensors 160 may detect the return of the item and transmit an indication of the item being return to the inventory management system 105. The inventory tracking and ordering component 125 may update the inventory based on the item being returned. Further, when new/replacement items are returned after an order, and the items are tagged (and the tags are associated with the items in the system), then the inventory may be updated. Further, upon return or arrival of tagged medical items, the system may recalibrate any active purchase orders in process for a location. That is, the ordering system may generate orders as items are used or assigned, and when items are delivered the system may recalibrate for the new items.

In some examples, the inventory tracking and ordering component 125 may monitor various item supply and usage levels during an extended period of time. The inventory monitoring may support smart inventory periodic automatic replenishment (PAR) levels and ordering. For example, the inventory tracking and ordering component 125 may determine that usage of a particular inventory item may increase during a season or month based on past data. Thus, the inventory tracking and ordering component 125 may increase the PAR level for that item for those time periods. Thus, the inventory tracking and ordering component 125 may support monitoring of average usage during various time periods to determine the dynamic PAR levels. In some examples, the inventory tracking and ordering component 125 may implement artificial intelligence/machine learning techniques to determine dynamic inventory adjustments. These techniques may receive inputs such as past usage data and PAR levels, medical facility population or bed usage, area (e.g., including multiple facilities) population and/or bed usage, demographic data, traffic data, and other types of data.

These aspects of inventory monitoring may support predictive analytics for various granularities. For example, based on monitoring of multiple inventory spaces and multiple facilities, the inventory management system 105 may support recommendation of appropriate PAR levels per facility and per inventory space. Thus, the inventory management system 105 may transmit notifications or alerts to providers or facility administrators when PAR levels should be adjusted. These adjustments may be based on the monitored inventory and may be adjusted for various seasonal or need trends. As described above, artificial intelligence automation may be used to correct inventories and adjust inventories based on markets, current market conditions, product, and seasonal sales.

The various components of the inventory management system 105 and the client application 140 may be configured in the same computing systems or in various separate systems as described herein. It should be understood that such components are for illustrative purposes and may be configured in various different systems or combinations of systems. Further, these systems described herein may support warehouse management. That is, the sensors 160 may be implemented in warehouses with various inventory spaces 110. The systems may track users within the warehouses and inventory spaces 110 to identify removal of items, generate and transmit alerts, support assignment of items to other resources (e.g., to shipping resources and the like), and other features as described herein. For example, the system may detect that a user has removed an item from a shelf, assign the item to the user. The user may then have the ability to assign the item to an order or shipment (e.g., similar to assigning an item to a patient by a clinician) using a device such as a tablet. This item assignment may be an example of an encounter. Thus, these systems may support warehouse inventory management, resupply, lost items, and other aspects of supply chain management.

Further, aspects of the disclosure described herein may support inventory management for multiple inventory spaces 110 in multiple facilities. Thus, the system provides an inventory management at the inventory space 110 level, facility level, and multiple facility level. Thus, aspects described herein are utilized in various levels of inventory.

As discussed herein, the client application 140 and inventory management system 105 may support various levels of access, which may be depend on the user. The client application 140 may display a dashboard, which may be configured according to the access level. For example, the dashboard for administrator of the inventory management system 105 (e.g., an inventory management services provider administrator) may display operational information, alerts, purchase orders, status, status of orders, missing equipment, etc. for all the facilities or multiple facilities that the service provider supports. That is, the administrator may view information associated with any, all, or a subset of facilities that the provider supports. Further, a provider administrator may view information associated with multiple facilities that the provider supports, and may filter based on the facility, inventory spaces within the facility, etc. Yet further, a facility administrator may view information associated with a facility. More particularly, the facility administrator may view inventory, order status, alerts, missing items, assigned items, encounter information, etc. associated with the facility and may filter such information based on various inventory spaces 110, particular types of inventory, etc. Lastly, a manufacturer supplier may view inventory, product characteristics, cost, freight, usage trends, replenishment rates, inventory turns, labels, etc. across all providers and closets as applicable to service the inventory management system and its clients.

Figure 2:
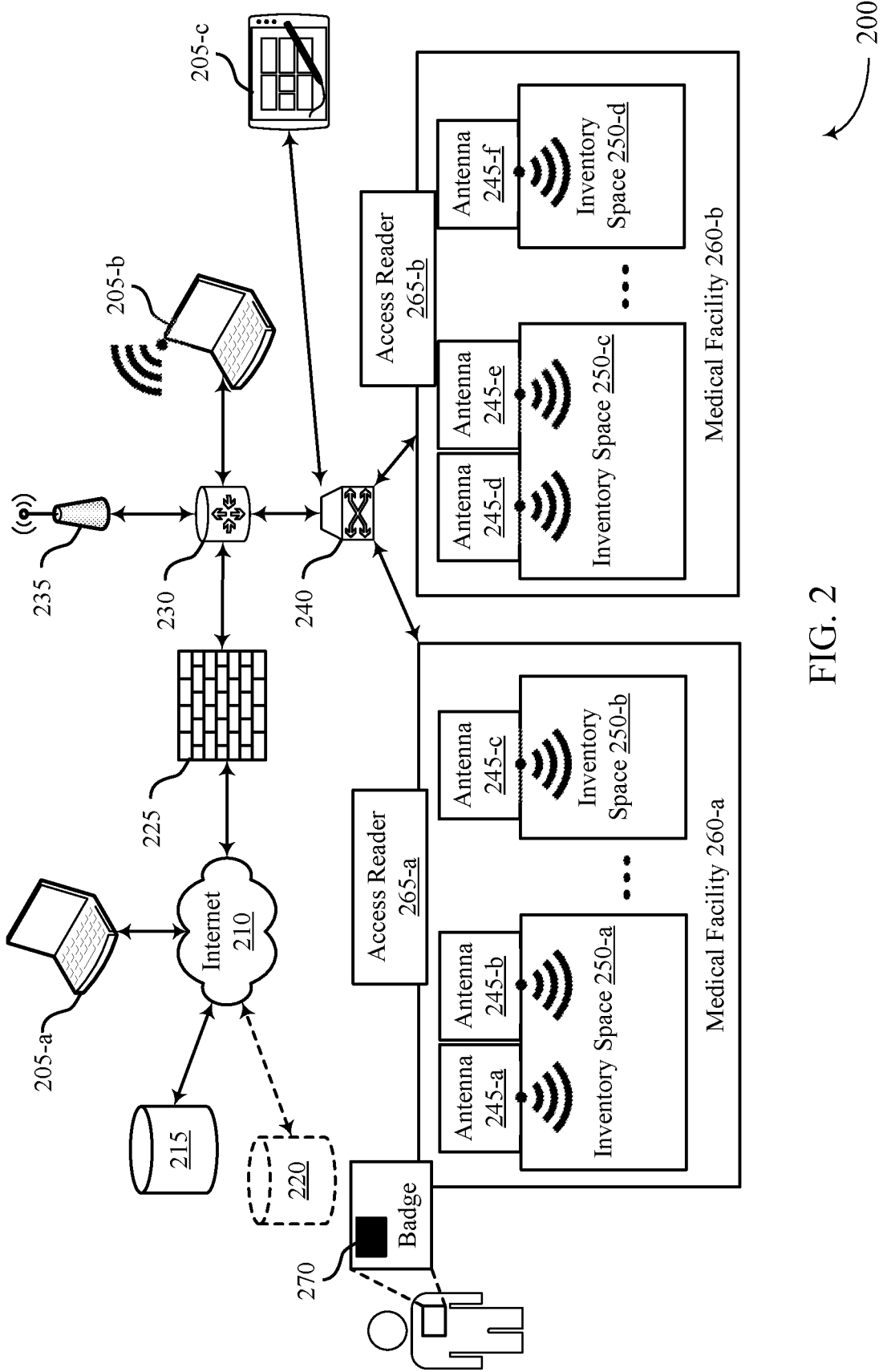
FIG. 2 illustrates an example system that supports inventory management in accordance with aspects of the present disclosure.

FIG. 2 illustrates an example system 200 that supports inventory management in accordance with aspects of the present disclosure. The system 200 includes various communication components and related systems for supporting inventory management. The system includes user devices 205, which may be utilized to configure the inventory management system, monitor various aspects of inventory, place and confirm orders, prescribe medical items, etc., as described herein. For example, a user may access an application or browser on the user device 205 to perform various features in the inventory management system. In some examples, a user may access data associated with inventory in medical facilities 260 using user device 205-*a*. The user device 205-*a* may be configured to access a firewall 225 of the medical facilities 260 using internet 210 resources. In some cases, the inventory management system maintains an enterprise zone manager server 215 and an optional redundant enterprise zone manager server 220.

User devices 205-*b* and 205-*c* may be an example of a device of the medical facilities 260-*a* or other facilities, which may be used by clinicians or other users to track inventory, assign inventory, prescribe inventory, initiate billing procedures, receive payments, etc. as described herein. The user device 205-*a* may access a network of the medical facility 260 using a wireless router 235 (e.g., access point). Another router or switch 230 may direct various communications within the intranet or network of the medical facility 260-*a*. A wired or wireless point of entry (POE) switch 240 may route communications between various antennas 245, access readers 265, and related components within the network of the medical facility 260-*a*.

The antennas 245-*a* may be examples of RFID readers, cameras, and the like, which may be used to monitor respective inventory spaces 250 to determine removal of medical items, return of medical items, etc. The antennas 245 may be configured to communicate according to wired or wireless communications protocols. For example, the antennas 245 may be examples of Wi-Fi antennas that are configured to communicate RFID data within the network of the medical facility 260. Thus, the user devices 205-*a*, servers, and related components may access the RFID data to support inventory monitoring and management described herein. The antennas 245-*a* may be positioned in inventory spaces 250 to monitor the inventory and such positioning may include entry and exit points, inventory shelves or drawers, etc. Access readers 265 may monitor access to the inventory spaces and may be examples of ID card readers, RFID readers, keypad entries, biometric readers, cameras, and the like. In some examples, an access readers 265 may detect an RFID tag 270 on a user (e.g., a badge of a user) to determine an identify of a user removing an item from an inventory space 250.

In some examples, the RFID system described herein uses RFID tags (e.g., attached to the inventory items) that are passive. That is, the RFID tags may not have an internal power source and may be powered by the signal transmitted by the RFID reader (e.g., antennas 245-*a*. However, it should be understood that the system may implemented active RFID tags that have an internal power source for broadcasting their signal that may be detected by the RFID readers (e.g., antennas 245-*a*).

Figure 3:
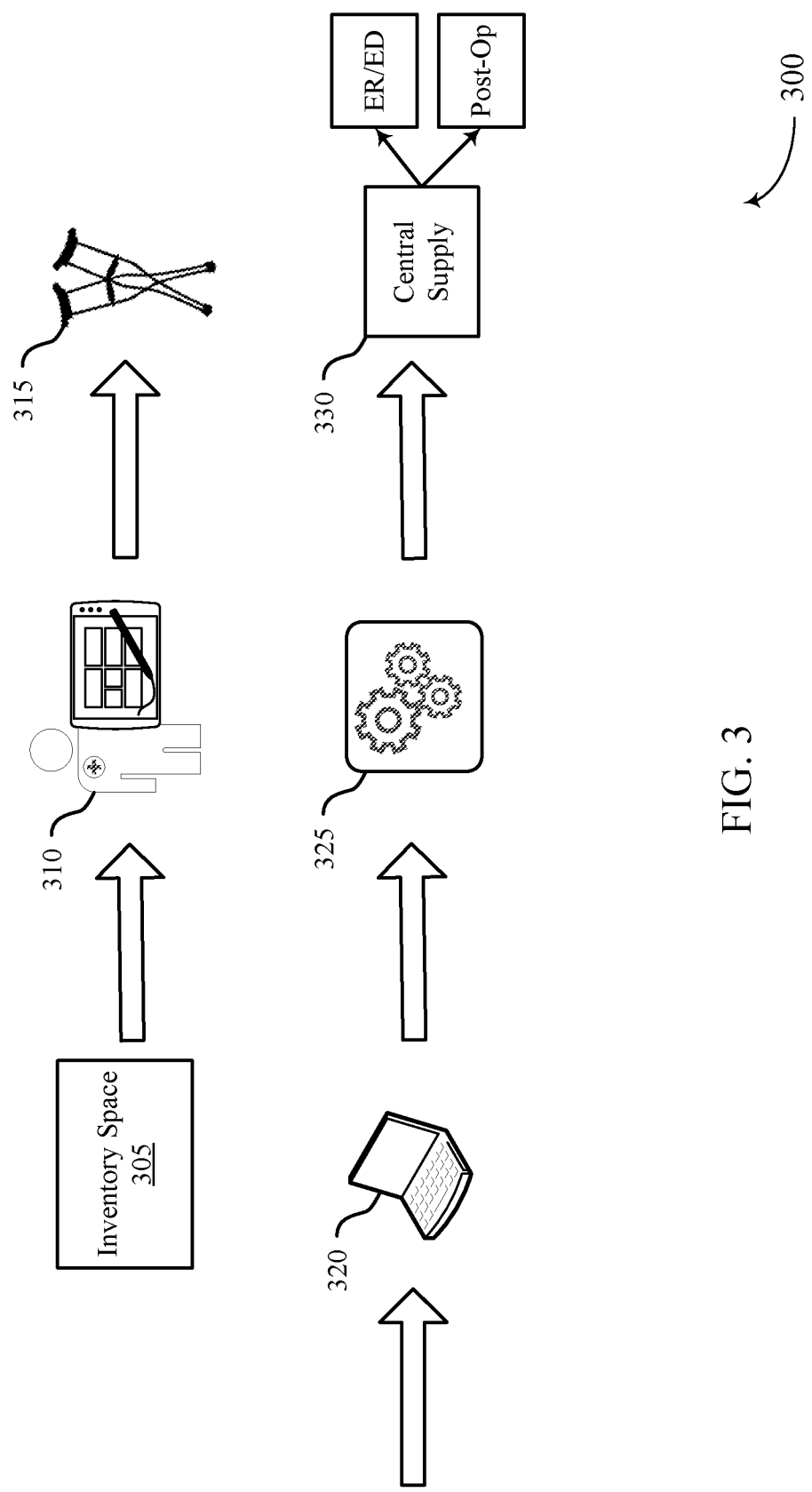
FIG. 3 illustrates a process flow diagram for a system that supports inventory management in accordance with aspects of the present disclosure.

FIG. 3 illustrates a process flow 300 supporting inventory management in accordance with aspects of the present disclosure. Various aspects of the process flow 300 may be performed by various entities and supported by the inventory management system as described herein. An inventory space 305 may contain medical items which may be assigned to patients. In some examples, the inventory space 305 may contain other items and may be an example of an inventory space in an environment other than a medical facility, such as a warehouse. A clinician may enter the inventory space, and the system described herein may recognize the clinician by the RFID tag of the clinician, the keypad entry, an ID card reader, or the like. In one example, the RFID tag is a sticker on the key or badge of the clinician. The clinician may use a tablet or other computing device that supports the inventory management system described herein as well as one or more medical items. The system thus assigns the medical items to the clinician.

At 310, the clinician may query the inventory management system for a patient using a user device supported by the systems described herein. The device may return the patient data via an API response. In some examples, the clinician may enter the patient data at the device. The clinician may complete an order, and the system may issue a prescription if the order has not been created in an electronic medical records system maintained by the facility. The physician may sign the electronic order on the device, using a text link for example.

At 315, the patient may be fitted with a medical item (e.g., DME) and the item is thus physically transferred to the patient. At 320, the insurance may be verified, and the copay calculated using the user device and application supported by the inventory management system described herein. Thus, the assigned medical item is assigned to a sales order.

The patient may agree and sign the delivery ticked on the device and pay the copay through the device.

At 325, the inventory management system may analyze the inventory by SKU, closet, and facility. The system may issue/order new supplies using electronic data interchange (EDI). The system may consider freight limits, order deadlines, PAR levels, etc. in determining whether to order products. In some cases, the system issues alerts to various parties indicating orders relative to freight limits or impending deadlines.

At 330, a central supply of the medical facility may be used to replenish the inventory spaces (e.g., closets). The closest may be examples of emergency room closets or spaces, post-operation closets or spaces, and the like. As the items may be preconfigured with RFID tags, the RFID tags may create a near instant acknowledgement (e.g., based on detection by sensors) of the items. Thus, the inventory may be maintained through physical movement, without the burden of paperwork.

Figure 4A:
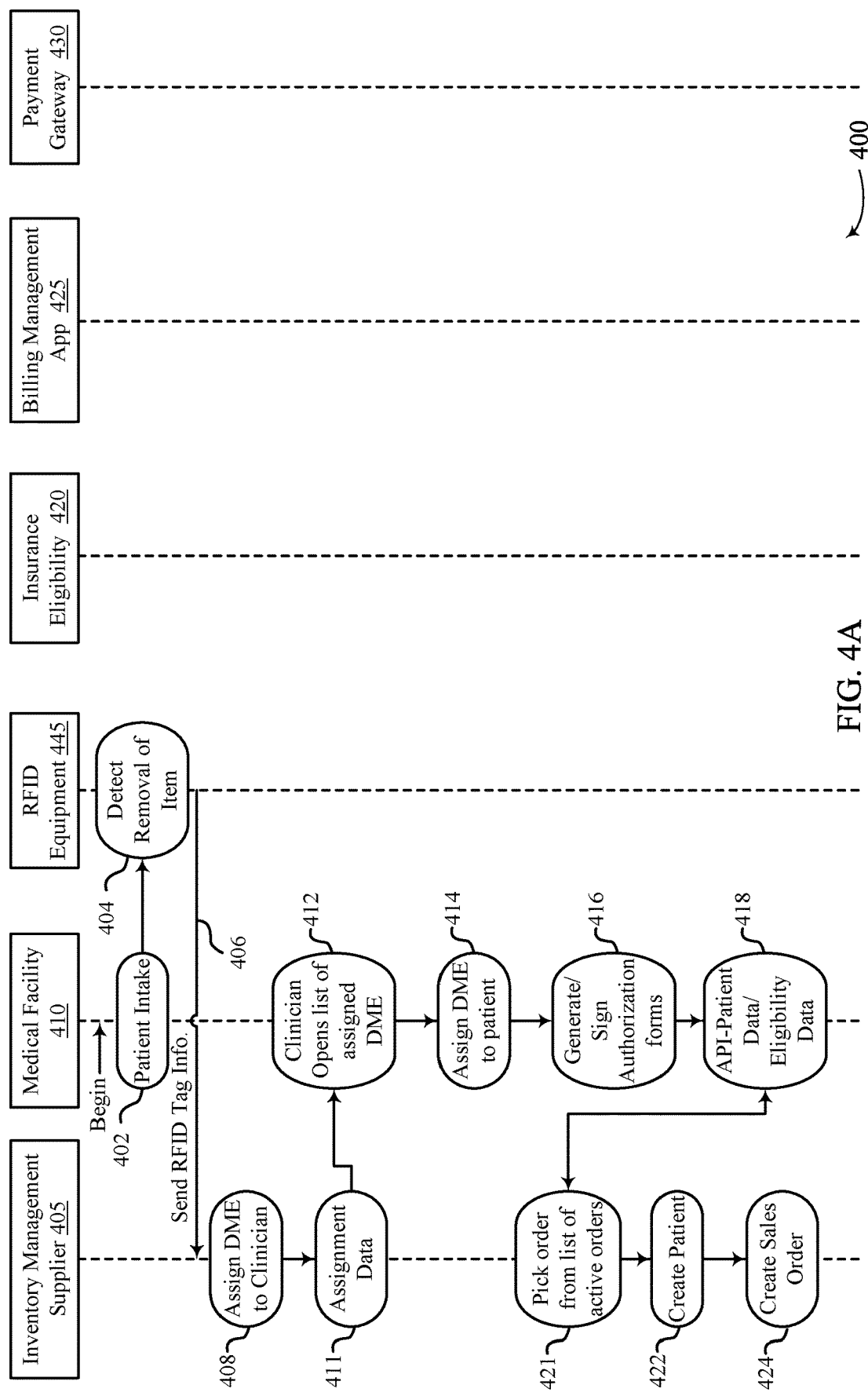
FIG. 4A and FIG. 4B are diagrams that illustrate example workflow and data tracking among an inventory management service supplier, a medical facility, RFID equipment, an insurance eligibility application, a billing management application, and a payment gateway.
Figure 4B:
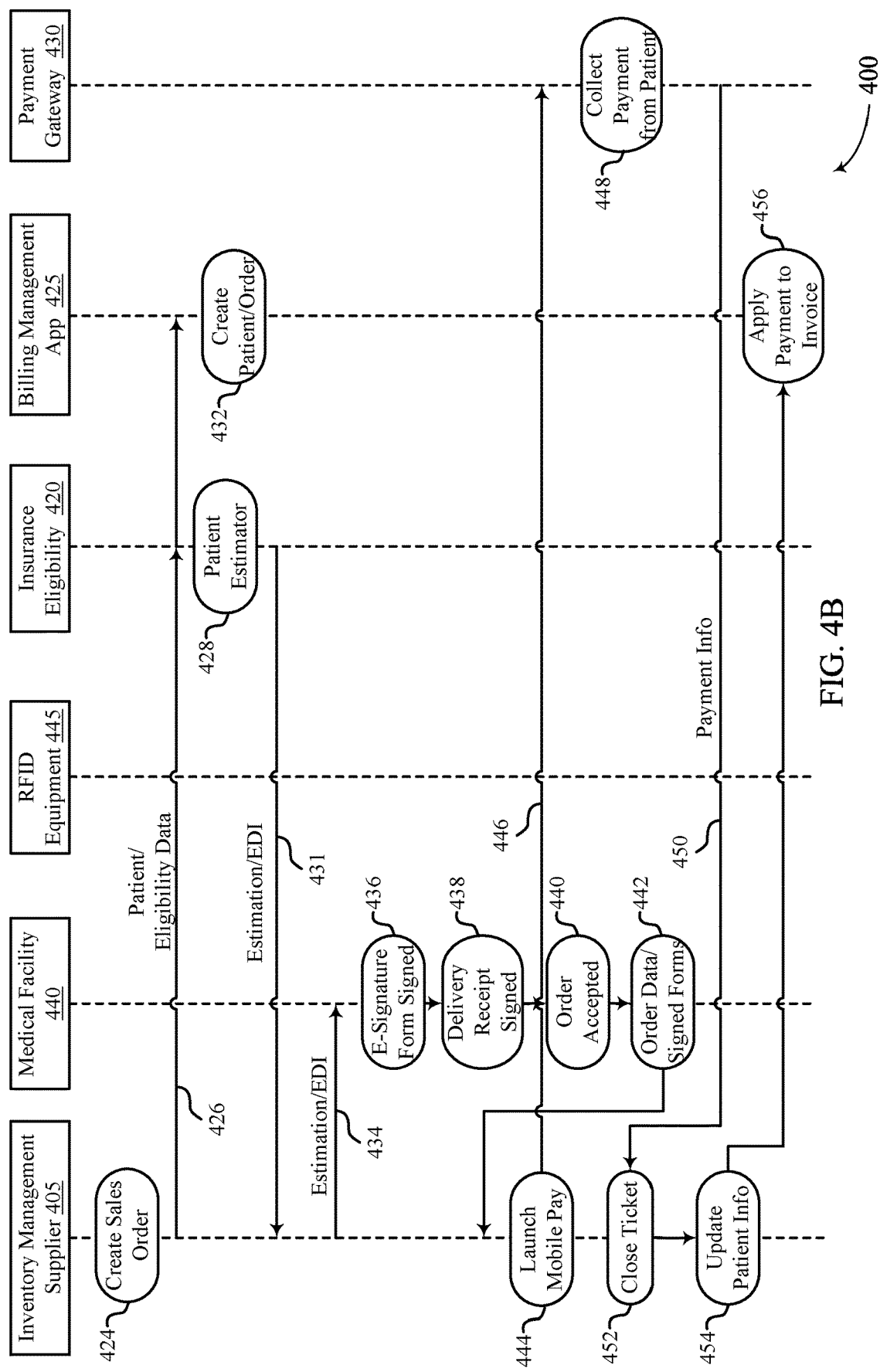

FIG. 4A and FIG. 4B are diagrams that illustrate example workflow and data tracking 400 in the disclosed technology. As shown in FIG. 4A and FIG. 4B, in some implementations, there are various systems and components in communication with each other in the disclosed inventory fulfillment system. The systems and components may include an inventory management services supplier 405, a medical facility 410, RFID equipment 415, an insurance eligibility application 420, a billing management application 425, and a payment gateway 430. In the disclosed technology, these various systems and components together achieve 1) inventory management; 2) order and document management; and 3) patient and financial management.

The inventory management may include inventory responsibility, real time stock status, real time par level management (e.g., facility, closet, SKU), EDI reorder/fulfillment with vendors, RFID technology in an open environment, open/shared closet inventory, vendor and manufacturer agnostic, camera—motion recording, real time facility alerts/visibility in the system, and closet security to prevent unauthorized shrinkage.

In some implementations, the order and document management may include electronic proof of delivery, patient e-signature, e-prescribing for a physician, and electronic compliance documentation.

In some implementations, the inventory management services supplier 405 supplies the inventory fulfillment solution to the medical facility 410, which may include an inventory management system (such as the inventory management system 105 of FIG. 1). The inventory management services supplier 405 initially sets up an inventory space within the medical facility 410, which contains medical items (e.g., DMEPOS items) individually tagged with RFID tags in communication with one or more RFID sensors within the inventory space. The medical items stored in the storage space may be supplied by a single medical item supplier or by multiple medical item suppliers. The inventory management services supplier 405, via the inventory management system, is in communication with the one or more medical item suppliers. The inventory management services supplier 405 provides suppliers with information received from the RFID sensors so that appropriate restocking of inventory may be made.

RFID technology uses RFID tags attached to the individual items, one or more RFID antennas which detect the presence of the RFID tag within a predetermined range, and RFID readers which communicate with the RFID antennas and record and transmit the associated data. The RFID readers can detect, capture, monitor and store information and status. One or more RFID antennas and the RFID readers that communicate with the one or more antennas are known together as RFID sensors.

RFID antennas sense the presence of RFID tags attached to medical items within the inventory space. When an RFID tag on a medical item is within range of an RFID antenna (e.g., 25 feet), the tagged item is designated as being in inventory. Conversely, when the RFID tag on an item is outside the range of an RFID antenna, the tagged item is designated as being removed from inventory. In this implementation, since the RFID tags identify the items to which they are attached, there may be no need to designate particular bins or locations for each item within the inventory space. RFID tags may function as intelligent bar codes that can communicate with a networked system.

In another implementation, two or more RFID antennas work in parallel with each other. For example, one RFID antenna may be mounted at the inventory space's entrance, such as on top of a door, and another RFID antenna may be located overhead in a central location of the inventory space. By communicating in parallel, the two RFID antennas may determine if a medical item tagged with an RFID tag is moving into or out of the inventory space. The RFID reader may communicate with up to four antennas. In one implementation, the storage space utilizes one RFID reader, two antennas, and an overhead camera.

The storage space can be secured by any known security means, and in some implementations, referred to above as the inventory room access control system. A clinician, labeled in FIGS. 4A and 4B as "Clinician," or other authorized user can enter credentials for gaining access to the inventory space. In one implementation, this is accomplished by swiping a magnetic stripe on an ID card through a card reader of the inventory space access control system. In the same or another implementation, this is accomplished by swiping a proximity card near a proximity reader. In the same or another implementation, this involves passing an RFID tag near an RFID antenna and associated reader. In the same or another implementation, this involves entering a code on a keypad. In the same or another implementation, this involves a retina scan or a thumbprint scan using a biometric scanning device. In the same or another implementation, this involves capturing an image of the user's face with a digital camera and processing the image using facial recognition software.

The inventory room access control system may comprise a keypad, magnetic stripe reader (card swipe), proximity reader, RFID tag reader, biometric sensor device, or other entry-access device that authorized customer personnel use to gain access to a medical product/supply inventory room. The inventory room may be a secured, limited-access location in the customer facility in which medical items are stored. In an implementation, the access control system communicates with the customer computer associated with the storage space via a wired or wireless network connection.

In some implementations, clinicians or otherwise authorized medical facility personnel that can access the inventory space, may have an RFID tag located on their person, such as on their ID badge. Once the user enters the storage space, the RFID antenna can sense the presence of the user inside the storage space. In this way, the RFID reader can associate the user of the storage space with the items removed or returned to the storage space.

In some implementations, a camera (e.g., an overhead camera) can be used in conjunction with the RFID system. This overhead camera may be a video camera (e.g., security camera) that is activated upon sensing motion. The overhead camera may be used to determine which user has removed which medical items if there are multiple users of the inventory space at the same time.

Using RFID tags on the users that have appropriate access to the storage space may eliminate the need to have separate security access means, such as biometric scans or magnetic swiping. In this implementation, the authorized users may be predetermined by an appropriate hospital administer and are outfitted with the RFID tags to be placed on their ID badges. If the RFID reader detects the removal of a medical item without detecting an RFID tag of any user, an appropriate alarm will sound alerting the unauthorized removal of one or more medical items. Similarly, if a camera or RFID reader detects removal without an authorized user being identified (e.g., using authorized access, as described above, using the camera, or other authentication process), an alert may be generated by the inventory management system and transmitted to appropriate users and systems.

In some implementations, the inventory sensors comprise one or more digital imaging devices, such as still cameras or video cameras, that capture images of items as the items are removed from or placed into the inventory space. In some implementations, each item is marked with a distinctive identifier, such as a bar code, quick-response (QR) code, or other symbol, that uniquely identifies the item. The imaging devices are positioned such that their field of view will encompass an area through which items may pass as the items are removed from or added to the inventory space. Movement within the field of view triggers the imaging devices to capture multiple images of the items, such that at least one of the captured images may show the distinctive identifier on each item. Software executed on the inventory management service supplier's one or more computers processes the image of the distinctive identifier (such as by "reading" the bar code or QR code) and provides identification information indicating which item is captured in the image.

In one implementation, an example method of the disclosed technology is initiated when a clinician begins a patient intake process at 402 at an appropriate user interface on a patient management system at the medical facility 410 (shown in block labeled "Patient Intake" in FIG. 4A). The Patient Intake information (described in detail above) will populate the EMR computer system of the medical facility 410, which may be associated with a patient database. The medical facility 410 may have a computer network that comprises an inventory room access control system, an EMR computer system, and a patient billing/claims application.

The medical facility computer network includes one or more customer computers that are associated with the storage space that is accessible by clinicians that have access to assign the medical items removed from the storage space. The one or more customer computers may be, for example, a desktop computer, laptop computer, tablet computer, or smart phone. A user input device, such as a keyboard or mouse or touchpad, may be provided as a component of the customer computer associated with the storage space. In some implementations, the customer computer is a removable electronic tablet that is an input device that is individually RFID tagged that includes the inventory management application that displays information regarding inventory transactions. In some cases, the display device and user input device are combined as a touch screen device.

In addition to removing medical items for multiple patients at a time, the inventory management application and system provided herein allows the user to remove multiple items for a particular patient at a time. For example, the clinician may not know what size the patient is going to require. Therefore, the inventory management application allows the clinician to remove multiple items in multiple sizes so that the clinician can appropriately fit the patient with the needed medical items and return the unused items to the storage space. When the items are returned, the status associated with the item may be updated to "on-hand," and the inventory appropriately updated.

Inventory management applications previously required that the clinician assign the medical items to the patient at the time of removal. In reality, this may not be possible because of the sizing issue discussed above. Additionally, it may not be possible to assign the items to an individual patient at the time of removal because a clinician may be tasked with removing medical items for a set of patients at a time. For example, a nurse may remove multiple sizes of braces, slings, crutches, and other medical equipment for various morning orthopedic operations. Once the patients have been provided with the necessary medical items, the medical facility 410 needs to have an inventory management application that allows the clinician to continue the process of assigning the medical items to the patient at a later time (after leaving the inventory space), such as in a patient's room.

In some implementations, the inventory space includes one or more input devices that are tagged with a unique RFID tag that the user also removes with the removal of one or more medical items. Therefore, upon leaving the range of the antenna of the RFID equipment, the RFID reader records medical items, an input device, and a user together and send that information to the inventory management service supplier. In some examples, the RFID reader, other sensors such as a camera or door authentications system, transmits an indication of the removed items (e.g., RFID tag information) and an identity of the user to the inventory management system.

After leaving the storage space, i.e., in an operating room, in a patient room, or in any other location within the medical facility, using the input device, the clinician may then access the list of medical items that have been assigned to the clinician that the clinician has removed. The clinician may then select the items to be assigned to each individual patient.

Once the appropriate demographic and insurance information has been entered at Patient Intake and the appropriate authorization has occurred to access the storage space, the Clinician may remove one of more medical items from the storage space.

Once one or more tagged items are moved outside the storage space at 404, the RFID reader communicates from the RFID Equipment 415 that the clinician has moved a medical item from the storage space. That communication is sent to the inventory management services supplier 405 at 406. The information included in this communication may include at least the identity of the clinician read from an RFID tag on the clinician's ID badge, and the identification of items removed. Based on which RFID reader has communicated with the inventory management service supplier, date and time of the removal and the storage space from where items are stored can be determined. Along with this communication may be the video capture (e.g., image capture) associated with the removal to be stored on the inventory management service supplier inventory system in case back up or reconciliation information is needed.

Information corresponding to the removal of the one or more items is received by the inventory management services supplier 405. The inventory management services supplier 405 assigns the medical item information to the Clinician at 408. Since the Clinician may be accessing the storage space to retrieve items for more than one patient at a time, the medical item information is not specific to a particular patient at this point. Next, at 411, the inventory management services supplier 405 creates a record of the assignment of the medical item to the physician, which may be an application program interface (API). This record/data is communicated back to the customer network (e.g., client application) in a format that can be accessed through the input device that the clinician has removed from the inventory space. Either in storage space or with the patient at the Medical Facility 410, the clinician opens a list of assigned medical item at 412.

In real time, still in the storage space, or at a later time in the storage space, or at another user interface within the customer's computer network, the Clinician may have the ability to access all the medical items associated with the Clinician. This may include all of the patients of the clinician for morning surgeries, for example. Interfacing with the medical facility's patient information, as stored in an EMR application, or in any other appropriate patient database, the Clinician next assigns the removed medical items to one or more patients at 414.

In another implementation, the user may manually enter the patient information into the input device that associates the patient with the removed medical items. The patient information would include patient demographics including insurance information.

In some implementations, the medical facility 410 may be using an e-prescription application. In this implementation, the input device may now access the e-prescription application and the patient information, which may be updated to include the medical items associated with the patient. In these and other implementations, accessing the EMR of the medical facility 410, the inventory management system software may create the equivalent of an e-prescription. At the patient's bedside, the Clinician may use the input device to generate authorization forms to be signed at 416. That is, the client application supported by the inventory management service supplier 405 may automatically generate forms for acceptance and signature based on the patient information, insurance information, item information, and the like.

The inventory management service supplier 405 may maintain a treatment protocol application, which lists medical items that may be ordered for treatment of the particular diagnosed injury. This information may be delivered to the Clinician on the input device (e.g., using the client application) at the time that the Clinician is assigning items to the specific patients. For example, for an orthopedic ankle injury, the treatment protocol application may display a listing of available ankle braces, ankle stirrups and walking boots. In some implementations, the items may be listed in groups according a product code, such as Healthcare Common Procedure Coding System (HCPCS) codes, Diagnosis Related Group (DRG) codes, or ICD coding, by way of examples.

Interfacing with the e-prescription application or the inventory management services supplier 405 or the Electronic Records or the Management Application or using the manually entered patient information, an API request may be created and transmitted at 418 In one implementation, as illustrated in FIG. 4A, this API request is communicated to the inventory management services supplier 405. The information may be communicated using an API request or other communication technique. In some examples, the information is communicated using secure communication protocols. In another implementation, one in which the customer handles the billing without the assistance of the inventory management services supplier 405, the customer generates the API request (or other data communication request) and interfaces with its own billing software provider or application. In FIG. 4A, this package of digital information is sent to the inventory management services supplier 405 and may include relevant information in which to later submit a claim to the patient's insurance provider, Medicare, or Medicaid for the medical items received.

The inventory management services supplier 405 may manage the customers' billing. The system may be managed by relevant and authorized inventory management services supplier personnel. The system user may receive the order information from the patient management system (or the client application) in the medical facility 410 based on the patient data/eligibility data at 421. The system may process any active order for billing.

Next, at 422, the system may create a profile for each patient to be billed to track billing information using the provided patient data from the clinician's input at the medical facility 410 such as into the input device. At 424, the system next creates a sales order for each patient and the items associated with the patient, which includes patient's insurance information.

Using EDI, an accepted standard of data submission according to known Medicare and Medicaid formats, the inventory management services supplier 405 sends eligibility data to the insurance eligibility application 420 or the billing management application 425, as illustrated at 426 in FIG. 4B.

In some implementations, the inventory management system may include an insurance eligibility application. The insurance eligibility application 420 can be a stand-alone company, part of the medical facility's capabilities, part of the inventory management services supplier 405 or a part of the billing management application 425. In FIGS. 4A and 4B, the insurance eligibility application is illustrated as a stand-alone component of the overall system. The insurance eligibility application 420 may include any known acceptable insurance clearinghouse database. The insurance eligibility application checks insurance information in real time using communication received from the inventory management services supplier at 428. In one example, the system described herein transmits an API request to the insurance supplier or aggregator and using the patient information to check the insurance information. Using the insurance eligibility application, information about a patient's eligibility and coverage for health insurance for a specific payer or health plan and the associated policy benefits is determined. The inquiry can be for a single date or for a date range. The insurance eligibility application 420 creates a response to communicate back to the inventory management services supplier 405 at 431.

The response is used to communicate the patient's eligibility status for coverage in the health insurance plan (or plans) for the requested date or date range. For each plan under which the patient is covered (for example, a medical plan and a dental plan), the response also provides details about the services which are covered; the benefits associated with those services; and financial information related to patient; for example: deductibles and remaining deductibles, co-pays, co-insurance, out of pocket amounts, exclusions, and limitations. The response may include other information pertinent to the patient's coverage, such as the patient's primary care provider and other payers under whom the patient may have coverage.

The response from the inquiry is sent back to the inventory management services supplier 405 at 431. Using the insurance eligibility application 420 and the inventory and management application of the present disclosure, the medical facility 410, using the client application described herein, can collect copays or other amounts that are the patients' responsibility before the patients are discharged from care.

The inventory management services supplier 405 communicates the "Patient/Eligibility Data" with the Insurance eligibility application 420 and with the billing management application 425 at 426. The billing management application 425 may create a patient and/or order at 432. The billing management application 425 may already be established with an existing supplier used by the medical facility 410. The inventory management services supplier 405 provides the data for the billing management application 425 to then further communicate onto the insurance provider.

In one example, the insurance eligibility application 420 handles the submission of the claim to the insurance provider and the inventory management services supplier 405, in real-time or near real-time, receives the co-payment information or patient's responsibility to the patient and processes the patient's payment in real-time or near real-time at the facility (e.g., the hospital).

As illustrated in FIG. 4B, the patient's payment responsibility with be presented to the patient at 434. At this time, payment may be accepted from the patient using an input device. In some implementations, the input device includes a credit card virtual terminal, which may be supported by or accessed by the client application associated with the inventory management application. A credit card or other type of payment processing application may be used to collect payment from the patient for their portion of the cost at the facility in real time. In some implementations, payment from the patient may also be processed using the medical facility's e-prescription application or an application supported by the inventory management services supplier 405. Other payment processes and systems are contemplated.

At the medical facility 410 of FIG. 4B, at 436, 438, and 440 the patient agrees to the delivery ticket, agrees to his copays and signs the delivery ticket, delivery manifest, or the like, using the application supported by the inventory management services supplier 405 and the input device. These forms may be generated in paper or electronically. This process may be repeated for multiple patients receiving medical items. The signed patient form is saved and stored on sight or in an associated computing system at 442. When the patient has agreed to pay their copay amounts at 440, the payment may be collected. In some examples, signed forms may be delivered to patient (e.g., via email address provided by patient).

The API request (or other communication) corresponding to the delivery ticket completed confirmation is sent to the inventory management services supplier 405 at 442. The inventory management services supplier 405 populates the copay amount in the credit card virtual terminal with copay amount and opens window of the virtual terminal to the patient in real-time or near real-time at the client application or associated application of the user device. The patient may then complete the credit card payment using the virtual terminal which may be running on the input device. Confirmation of payment is communicated back to the inventory management services supplier 405. The medical items now paid for by the patient are transferred to the patient. Further, the inventory management services supplier (or the application) may communicate confirmation that the copay is collected to the billing management system or application 425. This communication may also include delivery documents.

In one example, the medical facility 410 may not elect to have the inventory management services supplier 405 directly handle the collection of payments from the patients, such as described above, using a virtual credit card terminal in real-time or near real-time. This technique is illustrated at the bottom of FIG. 4B, which provides the functionality of collecting patient copays using Payment Gateway 430. This example begins at the inventory management services supplier 405 at 444. At 446, a communication may be sent to the Payment Gateway 430 with information the patients' payment responsibility. The Payment Gateway 430 may collect payment at 448, which includes credit card payment for the portion that is patient responsibility. In some implementations, this step may be a means of collection such as sending patients invoices via fax or mail or via a mobile pay application. Once payment is received, the Payment Gateway 430 may send payment confirmation back to the inventory management services supplier 405 at 450. With the payment received from the patient, the inventory management services supplier 405 may close the ticket at 452. The corresponding internal Patient Profile may then be updated with this payment information 454.

The inventory management services supplier 405 may update its billing application 425 regardless of which form of payment processing the medical facility 410 elects. The updated payment information may be transmitted to billing management application 425 so that the insurance claim information may be updated to reflect that patient's responsibility has been received at 456. The operations may be completed once payment information has been received from the patient and components have been notified of the payment.

Figure 5:
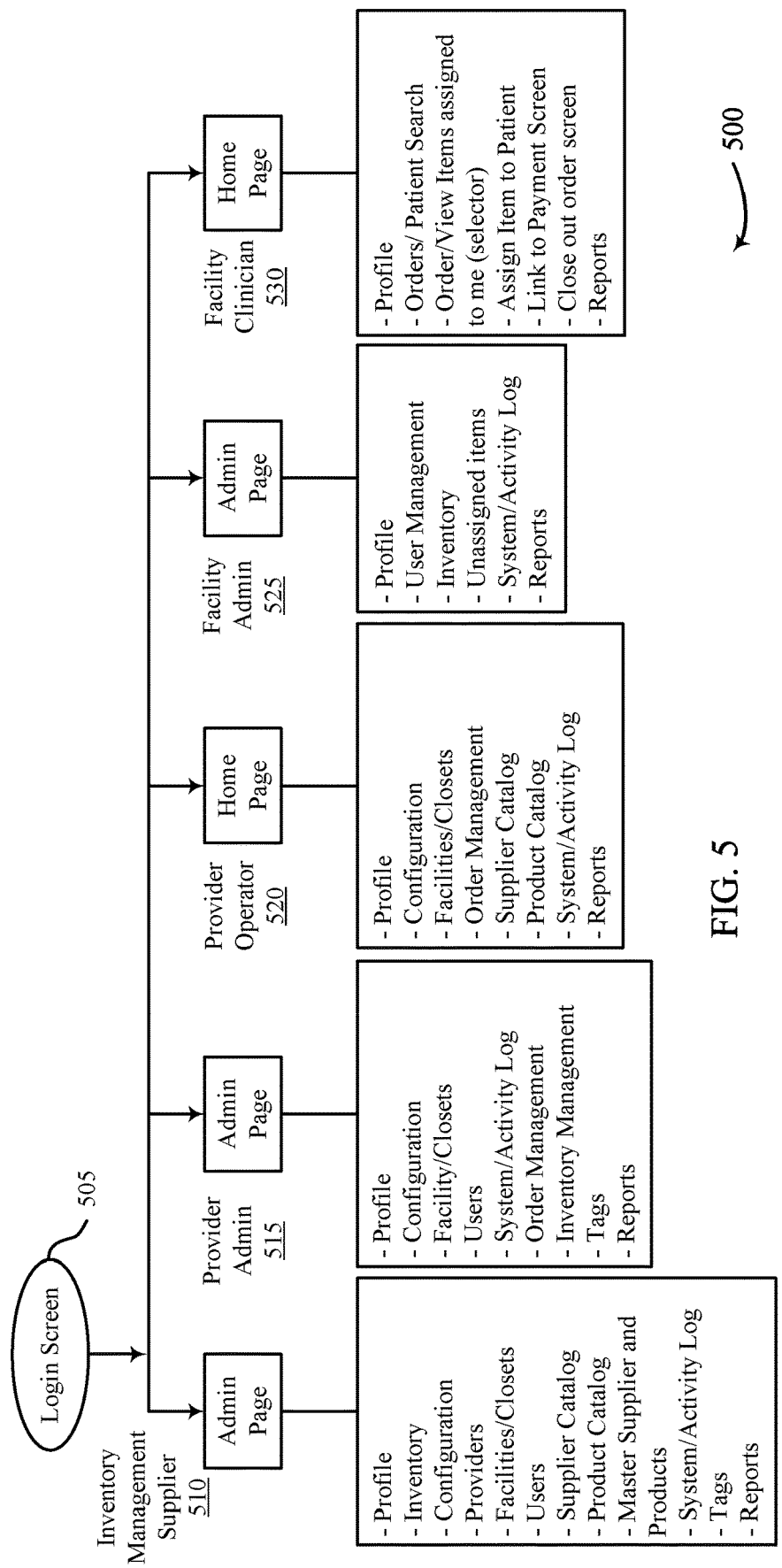
FIG. 5 is a block diagram that illustrates example user access to an inventory management system.

FIG. 5 is a block diagram that illustrates example types of user access 500 to the disclosed inventory management system. As shown, access to the inventory management system may be granted to various users, such as an Inventory Management Supplier (e.g., inventory management supplier 510), a Medical Item Provider Administrator 515 (e.g., an HME provider administrator), a Medical Item Provider Operator 520 (e.g., an HME provider operator), a Facility Administrator 525, and a Facility Clinician 530. The users described herein are examples of users, and other types of users granted access to the disclosed inventory management system are contemplated. Further the described access levels, services, pages, labels, and systems described with respect to FIG. 5 are examples, and other types of access levels, services, pages, labels, systems, etc. are contemplated within the scope of the present disclosure.

At the Login Screen 505, if a user has forgotten or does not know their password, the user can click on a forgot password link. The user may be taken to a forgot password screen, where the user can enter an email address and receive a link to a password reset operation. Once the user enters a correct username and password, the user may be directed to a home page or an administrative page with select features specific to that user based on their authorization.

The inventory management supplier (e.g., inventory management services supplier 105 of FIG. 1) 510 may have access to the system and may have access to the following features of the inventory management system: "Profile, Inventory, Configuration, Providers, Facilities/Closets, Users, Supplier Catalog, Product Catalog, Master Supplier and Master products, System/Activity Log, Reports." Starting with "Profile," each of the five different types of users illustrated in FIG. 5 may have the ability to update their own profile, including demographic, password, and other appropriate information. Next, the inventory management supplier 510 may have access to "Inventory." "Inventory" is the inventory tracking application (e.g., inventory tracking and ordering component 125) that is maintained by the inventory management services supplier for each of its client facilities (e.g., hospitals). Each time that one or more medical items are removed from the storage space in the facility, the inventory tracking application may be updated to reflect that removal. Appropriate replenishment of the medical items may be triggered if levels reach a threshold quantity of items.

An administrator of the inventory management supplier may be an example of a "global admin" that has access to features of the system described herein, since the inventory management supplier may interface with various parties and systems, such as suppliers, facilities, billing, insurance, and the like. For example, the global admin access the "Configuration" feature of the system in order to set up the appropriate users. The inventory management services supplier interfaces with the HME Providers, which are the manufacturers and suppliers of the medical items. The inventory management services supplier 510 also interfaces with the facilities. The global administrator may configure the "Providers" of the medical items, the "Facilities/Closets" that store medical items, and "Users," meaning the clinicians that are treating patients.

The inventory management system may also include functionality labeled "Supplier Catalog" which details the suppliers of the medical items and "Product Catalog" which details the medical items. The inventory management system may generate "System/Activity Log" to review its users' activity on the system and "Reports" which include, but are not limited to, inventory reports. The inventory management supplier 505 may also maintain a master supplier and product list.

The provider administrator 515 refers to a person at the supplier who may be in charge of setting up within its own company the persons to have access to the inventory management system. Multiple users with the supplier are contemplated as multiple sales agents or other personnel with the supplier will have various facility clients. The provider administrator 515 may have access to the following features of the inventory management system: "Profile, Configuration, Facilities/Closets, Users, System/Activity Log, Order Management, Inventory Management, Reports." The provider administrator 515 may access the configuration of the Facilities/Closets wherein the medical items are stored, retrieving real time information the quantities of its medical items at each facility location. The provider administrator 515 may also set up users within its own company at "Users." The provider administrator 515 may access the "System/Activity Log" to review its users' activity on the system. "Order Management" means that the supplier may access the purchasing and order information of its medical items to each facility. "Inventory Management" allows the supplier to access information related to the removal of medical items from the storage space in the facility and the inventory tracking application that may be updated to reflect that removal. "Inventory Management" also allows the user to set and review appropriate replenishment indicia for its items to the various facilities. Inventory adjustments may be communicated to the suppliers in order to replenish medical items in the storage space. Finally, the supplier may access "Reports" related to monthly billing, inventory tracking, and more.

At provider operator 520, sales agents and other relevant personnel within the supplier may have access to the inventory management system. The provider operator 520 may access the following features of the inventory management system: "Profile, Configuration, Facilities/Closets, Order Management, Supplier Catalog, Product Catalog, Inventory Management, System/Activity Log, Reports." The provider operator 520 may have most of the same ability to access the inventory management system as the provider administrator 515 with the exception that it may not be able to set up new users like the admin, and that it also has the ability to interface with the facilities, its own clients on the system using "Supplier Catalog", "Product Catalog," and "Inventory Management."

The facility administrator 525 may access the following features of the inventory management system: "Profile, User Management, Inventory, Unassigned Items, System/Activity Log, Reports." The facility administrator 525 manages the clinician users with the "User Management" feature. The facility administrator 525 may access the "Inventory" application as well is may likely be a purchasing agent or other suitable professional within the facility. The "Unassigned Items" corresponds to items that have been removed by a clinician that have not been assigned to a specific patient. The facility administrator 525 may use "Unassigned Items" to communicate with the clinician about assigning the medical item to a patient. The facility administrator 525 may access "System/Activity Log" and "Reports." The facility administrator 525 may manage the users within the facility, which may include designation of facility clinicians or other authorized users, which may be authorized to remove and assign items. The facility administrator 525 (and the facility clinician 530) may also access encounter data, which may indicate removal of items by clinicians and assignment of items by clinicians.

The facility clinician 530 may be a user that has direct access to patient information, in order to appropriate protect patient privacy. The facility clinician 530 may utilize the following features of the inventory management system: "Profile, Orders/Patient Search, Order View/Items assigned to me(selector), Assign Item to patient, Link to Payment Screen, Close out order screen, System Activity Log, Reports." The features of the system that the facility clinicians 530 may access were also discussed in reference to FIG. 4A and FIG. 4B. The clinician may conduct a patient search and assign medical items to a patient in real-time or near real-time while removing items from the storage space or the clinician may use the inventory management system to assign medical items to particular patients at a later time using the "Order View/Items assigned to me(selector)" feature of the system. The clinician may link medical items to a patient and then initiate the billing process with the "Link to Payment Screen" function. The clinician may "Close out order screen," access "System Activity Log" and "Reports."

These various users may further have access to tag data, which may be RFID tags. The user may use these features to assign tags to items (e.g., associate a tag identifier to an EPC or other item identifier). Thus, these features may be used to replace lost RFID tags, tag new items or replacement items, and the like. In some examples, the inventory management services supplier or item supplier may supply the tags and associated the tags within the system described herein. As such, when the items are delivered to the inventory space, the RFID readers may detect the tags and update the inventory accordingly.

Figure 6A:
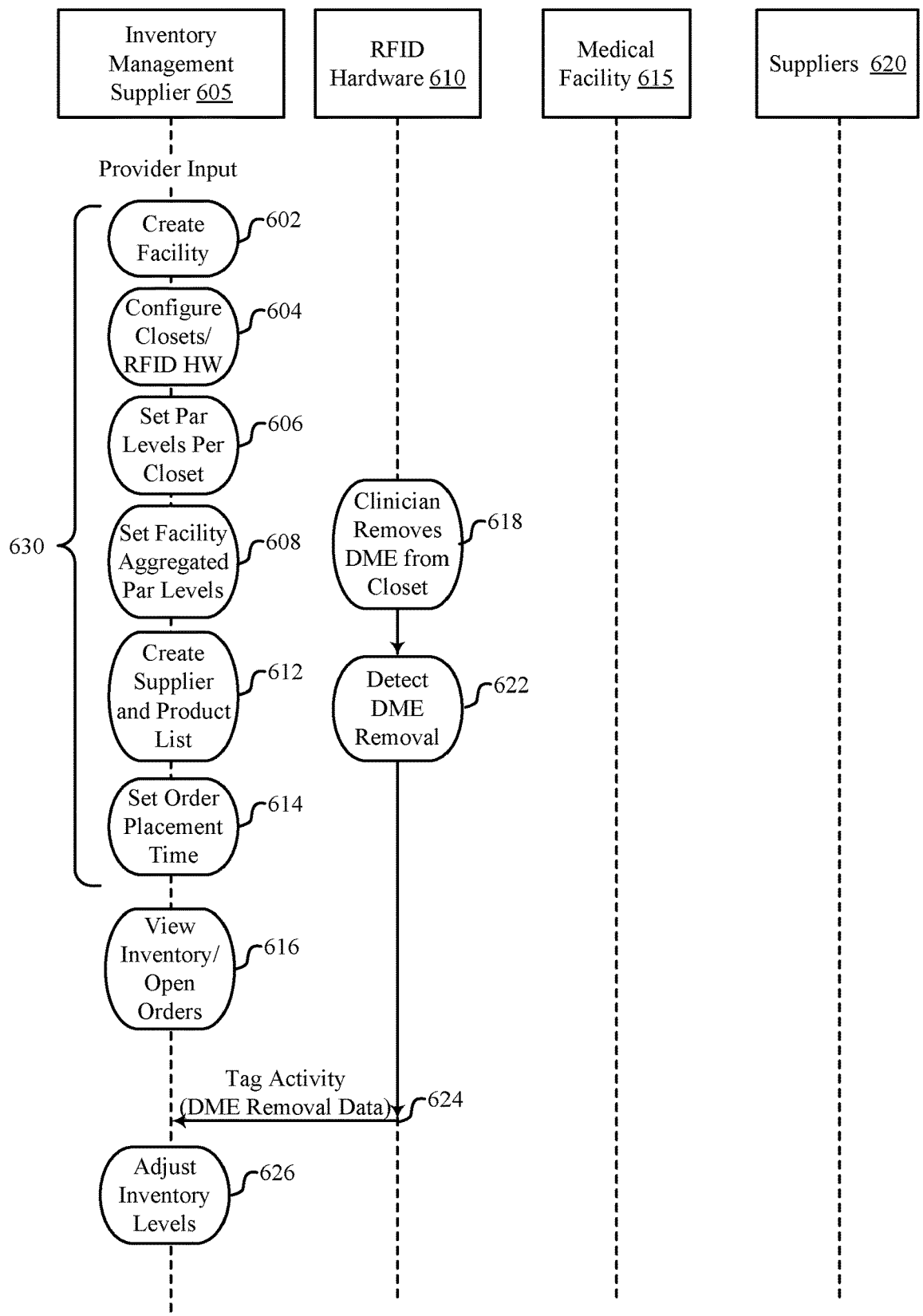
FIG. 6A and FIG. 6B are block diagrams that illustrate example set-up configuration process and example inventory management workflow in the disclosed inventory fulfillment system.
Figure 6B:
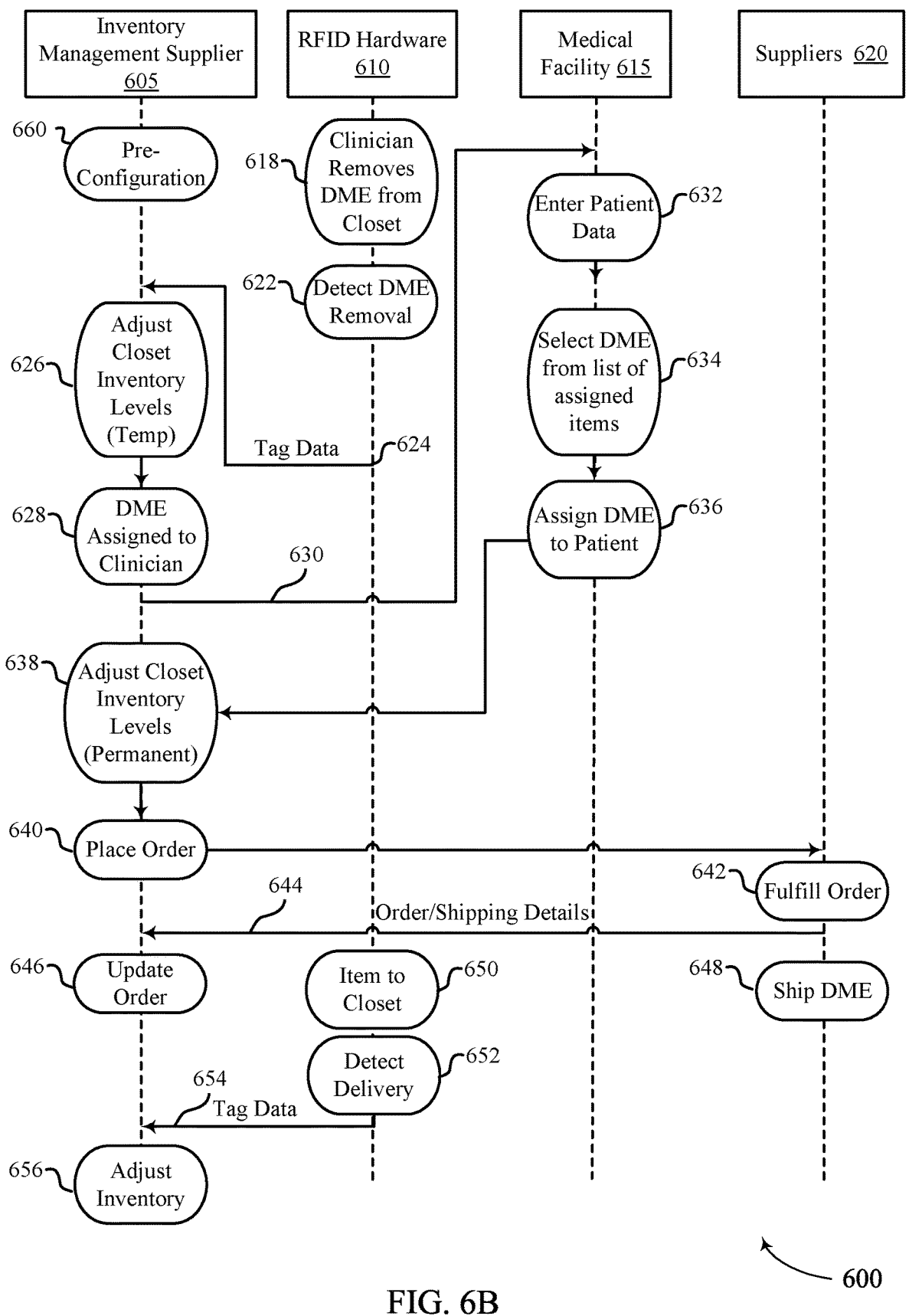

FIG. 6A and FIG. 6B are block diagrams that illustrate an example set-up configuration process and example inventory management workflow in the disclosed inventory fulfillment system. Specifically, FIG. 6A and FIG. 6B detail the initial set up or configuration of the storage space within each medical facility as well as the workflow 600, wherein a medical item is removed from the storage space is assigned to a patient.

The components of the inventory management system include: an inventory management services supplier 605, RFID equipment or Hardware 610, and a medical facility 615, (which may be examples of the corresponding components of FIGS. 1A and 1B), and suppliers 620. The storage space may be organized with DMEPOS or other inventory item supplier input, labeled as "Provider Input."

Referring to FIG. 6A, at initial configuration operations 630, the inventory management services supplier 605 may physically set up the storage space.

To create each facility at 602, there may be a need to physically build out a storage space, closet, or other suitable location for the medical supply items or other types of inventory items to be stored. The ordering settings may also be configured such that each medical facility interfaces with the inventory management services supplier 605 to determine the logistics of shipping, receiving, restocking, replenishment indicia, quantity thresholds, and any other details.

Once the storage space is physically built and outfitted with shelfing and storage bins, the closets may be stocked with medical items to be dispensed. At 604, the medical items may be RFID tagged, and the medical items tagged with RFID tags may be placed in the appropriate place within the storage space. The storage space may be configured with one or more RFID readers that may communicate with the individual RFID tags and with the inventory management services supplier. The one or more RFID readers may be examples of an overhead RFID reader in the storage space that counts the items as being in inventory if they are within some range and removed from inventory if outside of that range, as explained herein. The one or more RFID antennas of the reader's range may be selected based on the dimensions of the storage space so that removal from the storage space triggers the appropriate communication. The medical items may be supplied to the hospital facility already tagged with the RFID tags by the item suppliers, or conversely, they may be tagged by the RFID hardware supplier or by the inventory management services supplier.

Next, at 606, for each storage space within each medical facility, the par levels, including inventory replenishment indicia, may be set. The data for the par levels is configured in the inventory management application (e.g., the Inventory Management application discussed in FIG. 1).

Next, using the inventory management application, the inventory management services supplier may set the facility aggregated par levels at 608. Product and Supplier lists may be generated next at 612 so that the inventory in the storage space may be replenished with appropriate items from selected item suppliers (e.g., DMEPOS suppliers) at the appropriate times. In the inventory management system described herein, the storage space may hold inventory from multiple medical item suppliers. With input from both the medical item supplier and the medical facility, each medical item supplier may have its order placement times and details configured and saved in the inventory management application at 614, ending the initial configuration operations 630.

The inventory management services supplier 605 may physically inspect, maintain, access, restock, or otherwise view the inventory and the orders associated with the inventory on site or through the inventory management application at 616

Under RFID Hardware 610, the clinician may initiate the workflow of assigning a medical item to the patient with the removal of the medical item at 618, which may be detected by the RFID hardware 610 at 622. As explained above, the clinician may have properly accessed the storage space through known security means. As explained above, the clinician can remove multiple medical items at a time for multiple patients at his convenience and assign them to a patient in real-time or near real-time in the storage space or at a later time outside the storage space (e.g., in the patient's room).

In some cases, unused medical items may be returned to the storage space. The RFID sensors can detect the RFID tags being moved into its range. The input devices will also be returned to the storage space so that another user may use it. It is contemplated that any unused medical items that have been removed from the storage space that still have the RFID tag, may be returned to the storage space. The one or more RFID sensors may record that returned item as being returned to the storage space. The RFID sensor may communicate that return to the inventory management services supplier which may update the inventory management application with the returned item and may also update any unassigned item information associated with the clinician who originally selected the medical item and removed it from the storage space. It is contemplated that the RFID tag, much like a Universal Product Code, may be placed onto the medical items by the manufacturer or by the medical item supplier. It is contemplated that the RFID tag is a small tag and that it is not easily removed. If the clinician wants to return an item to the storage space that is unused, but it has its RFID tag removed or lost, the item may be placed in a designated space with the retagging to be performed by the medical item supplier or the inventory management services supplier. Once the item is retagged appropriately, the retagged item may be returned to storage space and the appropriate updates may be implemented in the system.

Additionally, adding items, such as a restocking or replenishment or in adding another medical item or supplier to the inventory space may be recorded by the one or more RFID sensors. The one or more RFID sensors read the tags of the new inventory items within its range and send that information to the inventory management service supplier in order to update the inventory application.

The antenna reads the removal of the medical item from the storage space once the item is moved beyond its range at 622. The RFID hardware may communicate with the inventory management services supplier at 624.

The removal data may be used to temporarily adjust the closet inventory levels at 626 in both FIG. 6A and in FIG. 6B. This is a temporary adjustment because the medical item is not yet assigned to a patient at this point.

Next, the inventory management services supplier 605 may assign the medical items removed to the clinician or user that has accessed the storage space at 628. Next, at 630, the inventory management services supplier 605 may communicate the Medical Item Assigned to Clinician to the patient management system (e.g., client application) being executed on the medical facility's 615 computer network. In some implementations, the transmitted data may be provided in an API request that may be recognized and compatible with the patient management system.

The Clinician either in real time, or at an earlier time may have entered the patient's data and it is stored on the EMR system of the facility's computer network at 632. Additionally, the patient data, including patient demographics and insurance information, may be manually entered at this time. The patient data from the EMR system or from the manual entry and the data received from the inventory management services supplier 605 allows the clinician to select specific medical item from a list of assigned items at 634. As another option, interfacing with an e-prescription application of the medical facility, the clinician can select a medical item from the list of assigned items. In the described implementations, whether patient data is pulled from any suitable patient database at the medical facility 615 or if it is manually entered, the inventory management services supplier 605 has created a list of assigned items that is presented on a suitable user interface of a user device for assigning those items to the users' patients (e.g., using a client application at a user or input device). Next, at 636, using an input device, the clinician can assign medical item to a patient.

At this point, the removed medical items may have been assigned to one or more patients. The medical facility can then initiate its billing/claims processing steps and interface with the insurance eligibility database as detailed in FIG. 4B. It may use the inventory management services supplier 605 for these steps as described in FIG. 4B or it may perform its own billing/claims processing steps.

On the inventory management flow depicted in FIGS. 6A and 6B, the next communication may be from the medical facility 615 to the inventory management supplier 605 and includes the assignment of the medical items to the one or more patients at 636. This data is used to adjust the closet inventory levels, at 638, on the inventory management service supplier's inventory management application/system.

Using the Par Levels established in the configuration steps above, the inventory management service supplier's inventory management application can place an order based on aggregated closet inventory/order placement times at 640. The inventory management service supplier's inventory management application may send the order to be placed to the appropriate supplier. The Suppliers (e.g., DMEPOS suppliers) 620 may receive and fulfill the order see block labeled at 642. Once the order for replenishment has been prepared and shipped by the Supplier 620 to the medical facility 615, the supplier 620 sends the details to the inventory management service supplier's inventory management application, at 644, so that the order can be tracked at 646.

The medical facility 615 receives the shipment. The medical items received by the hospital may be tagged with individual RFID tags. The supplier 620 delivers the medical items to the medical facility 615 at 648 and places it in the storage space in its appropriate designated space, bin, or shelf at 650. The RFID Antenna within the closet recognizes the newly received inventory at 652. The system may generate an account of the movement into the inventory space and sends that data to the inventory management services supplier at 654. The inventory management services supplier 605 receives the updated inventory adjustment and adjusts the closet inventory levels at 656.

In some implementations, the FIGS. 6A and 6B may be representative of a single medical facility 615 and a single Supplier 620 and that the system described herein may be scalable to any number of storage spaces in any number of medical facilities and with any number of suppliers.

Figure 7:
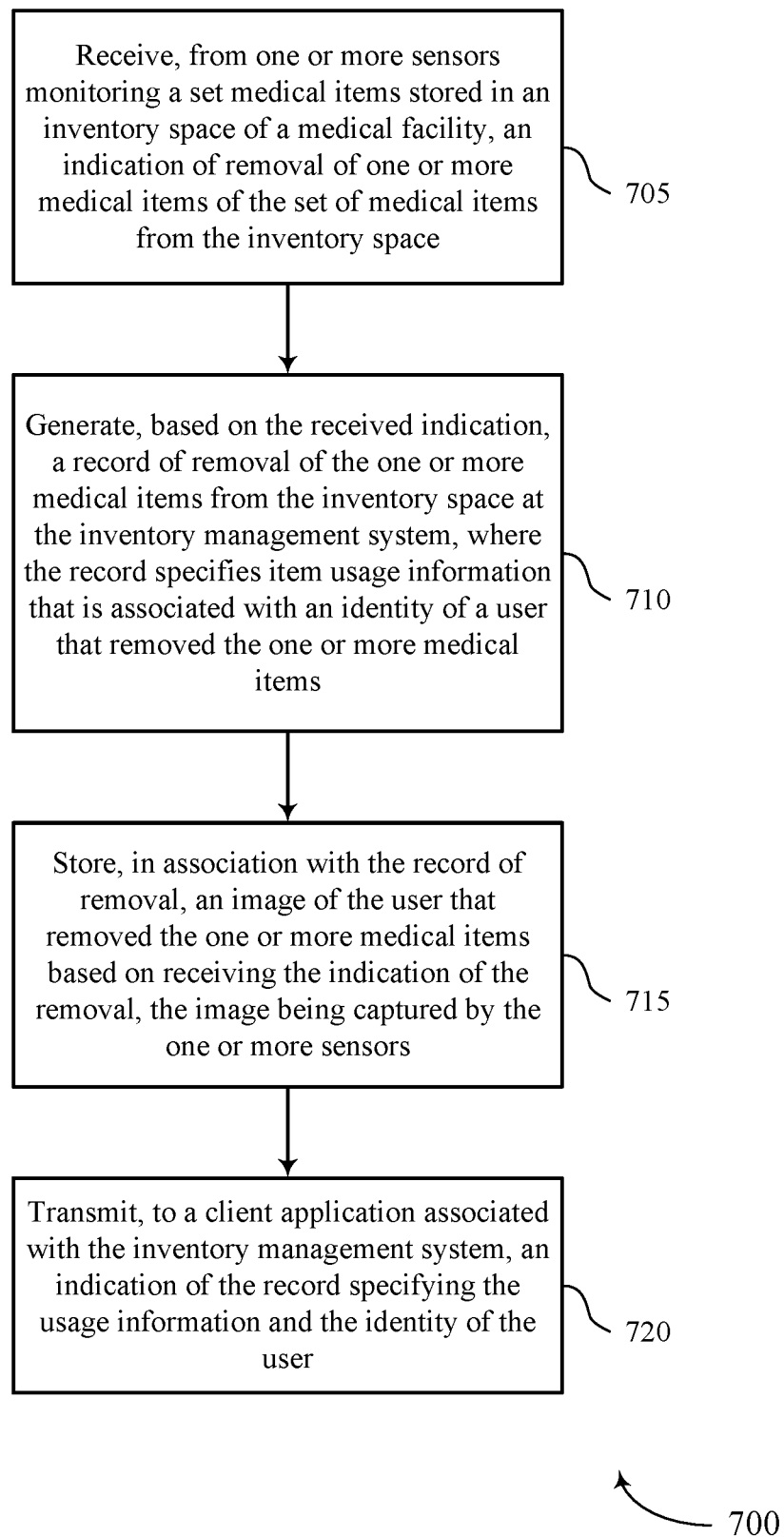
FIG. 7 illustrates a flowchart illustrating an example method that supports inventory fulfillment in accordance with aspects of the present disclosure.

FIG. 7 shows a flowchart illustrating a method 700 that supports inventory management in accordance with aspects of the present disclosure. The operations of method 700 may be implemented by an application server or its components as described herein. For example, the operations of method 700 may be performed by an inventory management system as described with reference to FIGS. 1 through 4. In some examples, an inventory management system may execute a set of instructions to control the functional elements of the inventory management system to perform the functions described herein. Additionally, or alternatively, an inventory management system may perform aspects of the functions described herein using special-purpose hardware.

At 705, the inventory management system may receive, from one or more sensors monitoring a set medical items stored in an inventory space of a medical facility, an indication of removal of one or more medical items of the set of medical items from the inventory space. The operations of 705 may be performed according to the methods described herein.

At 710, the inventory management system may generate, based on the received indication, a record of removal of the one or more medical items from the inventory space at the inventory management system, where the record specifies item usage information that is associated with an identity of a user that removed the one or more medical items. The operations of 710 may be performed according to the methods described herein.

At 715, the inventory management system may store, in association with the record of removal, an image of the user that removed the one or more medical items based on receiving the indication of the removal, the image being captured by the one or more sensors. The operations of 715 may be performed according to the methods described herein.

At 720, the inventory management system may transmit, to a client application associated with the inventory management system, an indication of the record specifying the usage information and the identity of the user. The operations of 720 may be performed according to the methods described herein.

Figure 8:
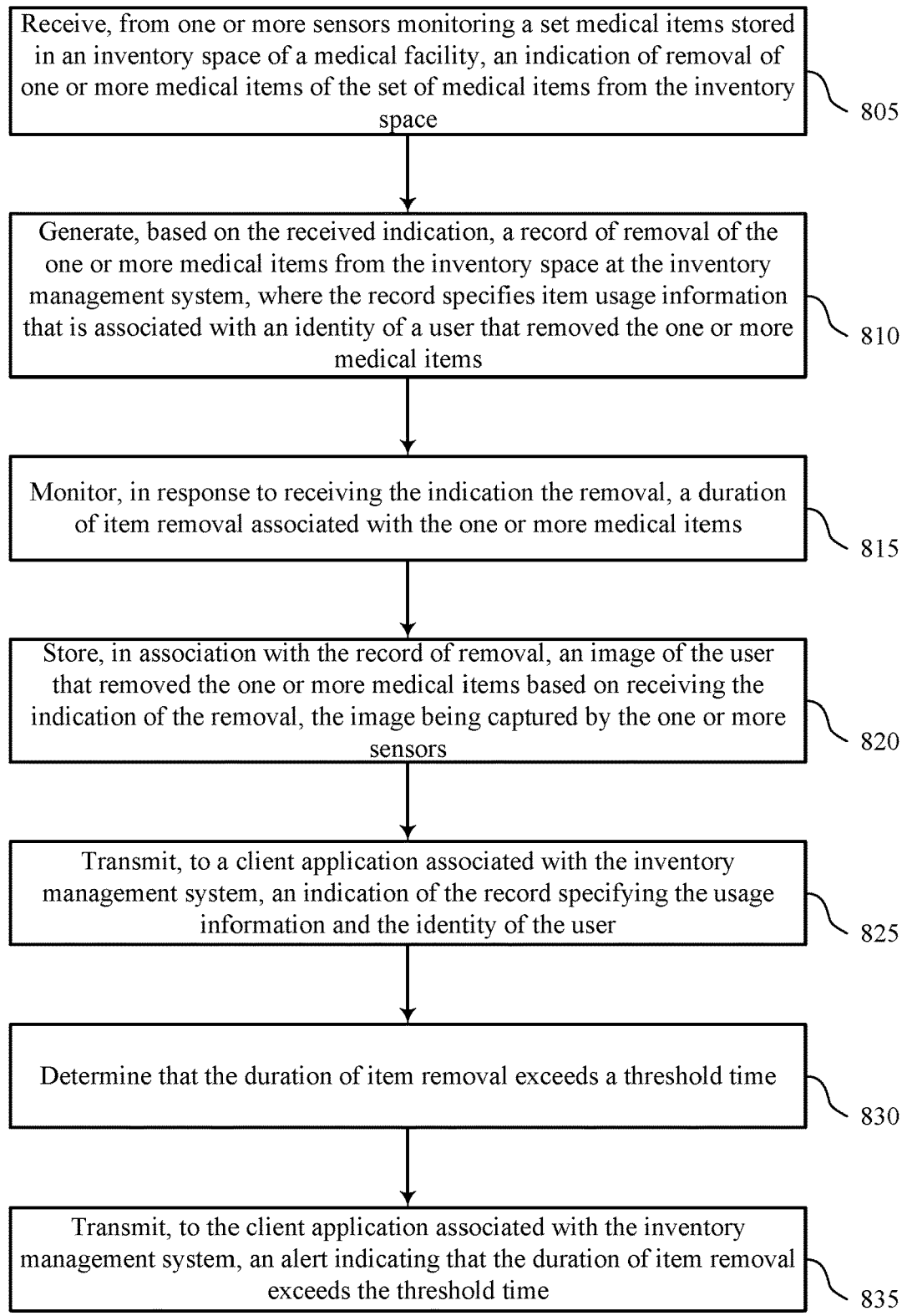
FIG. 8 illustrates a flowchart illustrating an example method that supports inventory fulfillment in accordance with aspects of the present disclosure.

FIG. 8 shows a flowchart illustrating a method 800 that supports inventory management in accordance with aspects of the present disclosure. The operations of method 800 may be implemented by an application server its components as described herein. For example, the operations of method 800 may be performed by an inventory management system as described with reference to FIGS. 1 through 4. In some examples, an inventory management system may execute a set of instructions to control the functional elements of the inventory management system to perform the functions described herein. Additionally, or alternatively, an inventory management system may perform aspects of the functions described herein using special-purpose hardware.

At 805, the inventory management system may receive, from one or more sensors monitoring a set medical items stored in an inventory space of a medical facility, an indication of removal of one or more medical items of the set of medical items from the inventory space. The operations of 805 may be performed according to the methods described herein.

At 810, the inventory management system may generate, based on the received indication, a record of removal of the one or more medical items from the inventory space at the inventory management system, where the record specifies item usage information that is associated with an identity of a user that removed the one or more medical items. The operations of 810 may be performed according to the methods described herein.

At 815, the inventory management system may monitor, in response to receiving the indication the removal, a duration of item removal associated with the one or more medical items. The operations of 815 may be performed according to the methods described herein.

At 820, the inventory management system may store, in association with the record of removal, an image of the user that removed the one or more medical items based on receiving the indication of the removal, the image being captured by the one or more sensors. The operations of 820 may be performed according to the methods described herein.

At 825, the inventory management system may transmit, to a client application associated with the inventory management system, an indication of the record specifying the usage information and the identity of the user. The operations of 825 may be performed according to the methods described herein.

At 830, the inventory management system may determine that the duration of item removal exceeds a threshold time. The operations of 830 may be performed according to the methods described herein.

At 835, the inventory management system may transmit, to the client application associated with the inventory management system, an alert indicating that the duration of item removal exceeds the threshold time. The operations of 835 may be performed according to the methods described herein.

Figure 9:
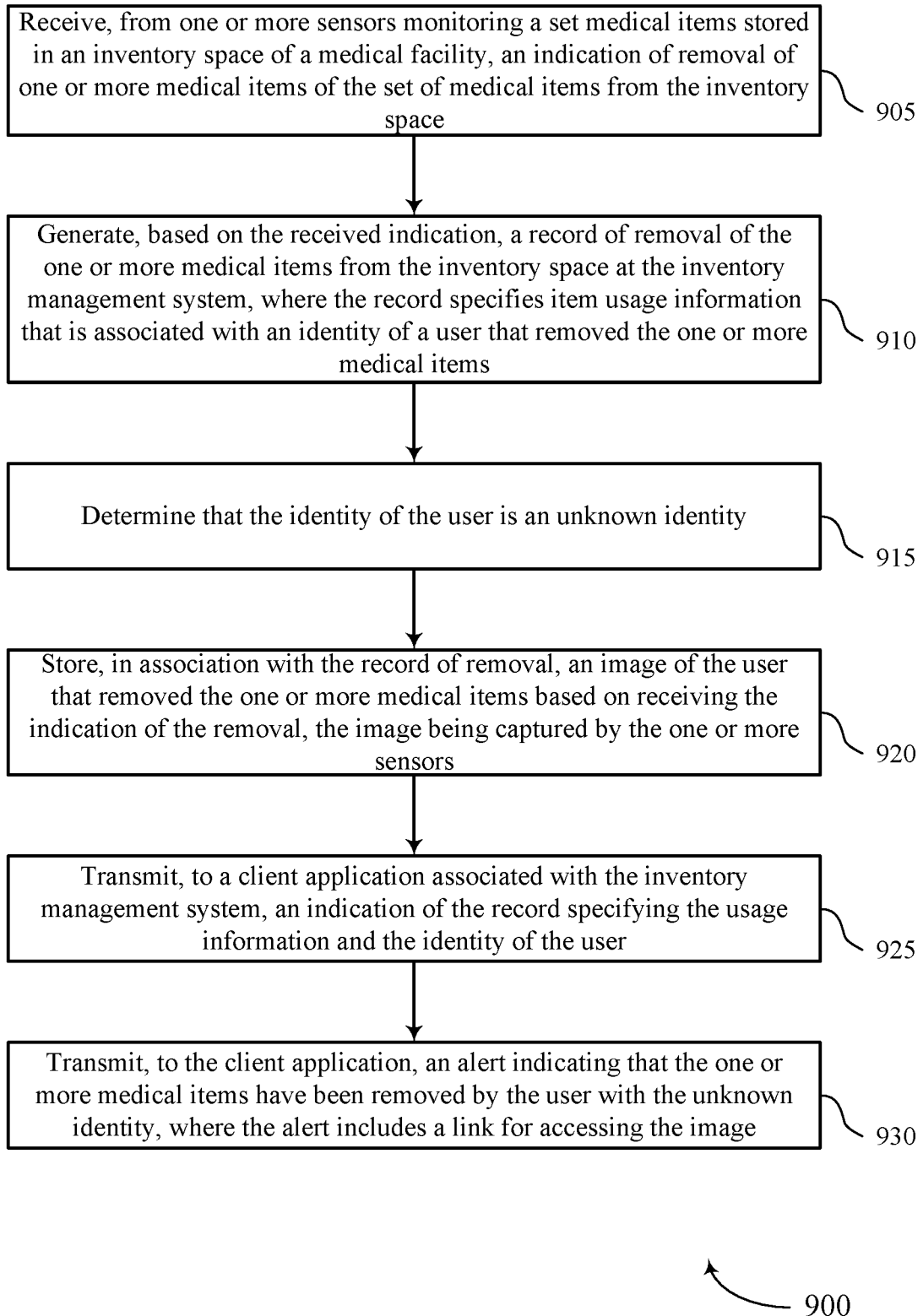
FIG. 9 illustrates a flowchart illustrating an example method that supports inventory fulfillment in accordance with aspects of the present disclosure.

FIG. 9 shows a flowchart illustrating a method 900 that supports inventory management in accordance with aspects of the present disclosure. The operations of method 900 may be implemented by an application server or its components as described herein. For example, the operations of method 900 may be performed by an inventory management system as described with reference to FIGS. 1 through 4. In some examples, an inventory management system may execute a set of instructions to control the functional elements of the inventory management system to perform the functions described herein. Additionally, or alternatively, an inventory management system may perform aspects of the functions described herein using special-purpose hardware.

At 905, the inventory management system may receive, from one or more sensors monitoring a set medical items stored in an inventory space of a medical facility, an indication of removal of one or more medical items of the set of medical items from the inventory space. The operations of 905 may be performed according to the methods described herein.

At 910, the inventory management system may generate, based on the received indication, a record of removal of the one or more medical items from the inventory space at the inventory management system, where the record specifies item usage information that is associated with an identity of a user that removed the one or more medical items. The operations of 910 may be performed according to the methods described herein.

At 915, the inventory management system may determine that the identity of the user is an unknown identity. The operations of 915 may be performed according to the methods described herein.

At 920, the inventory management system may store, in association with the record of removal, an image of the user that removed the one or more medical items based on receiving the indication of the removal, the image being captured by the one or more sensors. The operations of 920 may be performed according to the methods described herein.

At 925, the inventory management system may transmit, to a client application associated with the inventory management system, an indication of the record specifying the usage information and the identity of the user. The operations of 925 may be performed according to the methods described herein.

At 930, the inventory management system may transmit, to the client application, an alert indicating that the one or more medical items have been removed by the user with the unknown identity, where the alert includes a link for accessing the image. The operations of 930 may be performed according to the methods described herein.

Figure 10:
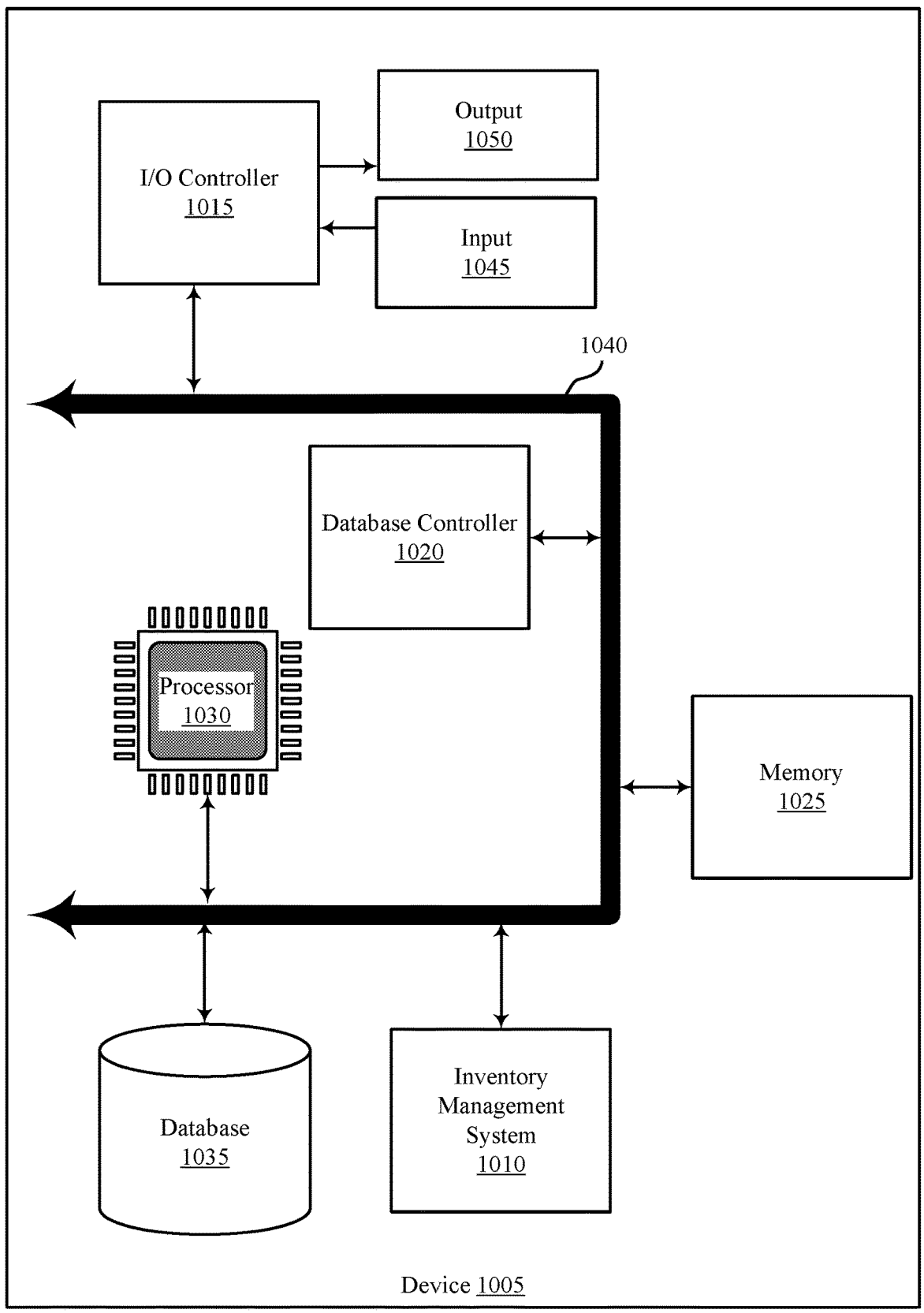
FIG. 10 is a block diagram that illustrates an example computing system that supports inventory fulfillment in accordance with aspects of the present disclosure.

FIG. 10 shows a block diagram of a system 1000 including a device 1005 that supports inventory management in accordance with aspects of the present disclosure. The device 1005 may be an example of or include the components of a user device 435 or an inventory management system 105 as described herein. The device 1005 may be an example of an application server, distributing computing system, analytical server, or other computing system as described herein. The device 1005 may include components for bi-directional data communications including components for transmitting and receiving communications, including an inventory management component 1010, an I/O controller 1015, a database controller 1020, memory 1025, a processor 1030, and a database 1035. These components may be in electronic communication via one or more buses (e.g., bus 1040).

The inventory management component 1010 may be an example of an inventory management system 105 as described herein. For example, the inventory management component 1010 may perform any of the methods or processes described above with reference to FIGS. 5 through 7. In some cases, the inventory management component 1010 may be implemented in hardware, software executed by a processor, firmware, or any combination thereof.

The I/O controller 1015 may manage input signals 1045 and output signals 1050 for the device 1005. The I/O controller 1015 may also manage peripherals not integrated into the device 1005. In some cases, the I/O controller 1015 may represent a physical connection or port to an external peripheral. In some cases, the I/O controller 1015 may utilize an operating system such as iOS®, ANDROID®, MS-DOS®, MS-WINDOWS®, OS/2®, UNIX®, LINUX®, or another known operating system. In other cases, the I/O controller 1015 may represent or interact with a modem, a keyboard, a mouse, a touchscreen, or a similar device. In some cases, the I/O controller 1015 may be implemented as part of a processor. In some cases, a user may interact with the device 1005 via the I/O controller 1015 or via hardware components controlled by the I/O controller 1015.

The database controller 1020 may manage data storage and processing in a database 1035. In some cases, a user may interact with the database controller 1020. In other cases, the database controller 1020 may operate automatically without user interaction. The database 1035 may be an example of a single database, a distributed database, multiple distributed databases, a data store, a data lake, or an emergency backup database.

Memory 1025 may include random-access memory (RAM) and read-only memory (ROM). The memory 1025 may store computer-readable, computer-executable software including instructions that, when executed, cause the processor to perform various functions described herein. In some cases, the memory 1025 may contain, among other things, a basic input/output system (BIOS) which may control basic hardware or software operation such as the interaction with peripheral components or devices.

The processor 1030 may include an intelligent hardware device, (e.g., a general-purpose processor, a DSP, a central processing unit (CPU), a microcontroller, an ASIC, an field programmable gate array (FPGA), a programmable logic device, a discrete gate or transistor logic component, a discrete hardware component, or any combination thereof). In some cases, the processor 1030 may be configured to operate a memory array using a memory controller. In other cases, a memory controller may be integrated into the processor 1030. The processor 1030 may be configured to execute computer-readable instructions stored in a memory 1025 to perform various functions (e.g., functions or tasks supporting inventory management).

A method of data processing at an inventory management system is described. The method may include receiving, from one or more sensors monitoring a set medical items stored in an inventory space of a medical facility, an indication of removal of one or more medical items of the set of medical items from the inventory space, generating, based on the received indication, a record of removal of the one or more medical items from the inventory space at the inventory management system, where the record specifies item usage information that is associated with an identity of a user that removed the one or more medical items, storing, in association with the record of removal, an image of the user that removed the one or more medical items based on receiving the indication of the removal, the image being captured by the one or more sensors, and transmitting, to a client application associated with the inventory management system, an indication of the record specifying the usage information and the identity of the user.

An apparatus for data processing at an inventory management system is described. The apparatus may include a processor, memory coupled with the processor, and instructions stored in the memory. The instructions may be executable by the processor to cause the apparatus to receive, from one or more sensors monitoring a set medical items stored in an inventory space of a medical facility, an indication of removal of one or more medical items of the set of medical items from the inventory space, generate, based on the received indication, a record of removal of the one or more medical items from the inventory space at the inventory management system, where the record specifies item usage information that is associated with an identity of a user that removed the one or more medical items, store, in association with the record of removal, an image of the user that removed the one or more medical items based on receiving the indication of the removal, the image being captured by the one or more sensors, and transmit, to a client application associated with the inventory management system, an indication of the record specifying the usage information and the identity of the user.

Another apparatus for data processing at an inventory management system is described. The apparatus may include means for receiving, from one or more sensors monitoring a set medical items stored in an inventory space of a medical facility, an indication of removal of one or more medical items of the set of medical items from the inventory space, generating, based on the received indication, a record of removal of the one or more medical items from the inventory space at the inventory management system, where the record specifies item usage information that is associated with an identity of a user that removed the one or more medical items, storing, in association with the record of removal, an image of the user that removed the one or more medical items based on receiving the indication of the removal, the image being captured by the one or more sensors, and transmitting, to a client application associated with the inventory management system, an indication of the record specifying the usage information and the identity of the user.

A non-transitory computer-readable medium storing code for data processing at an inventory management system is described. The code may include instructions executable by a processor to receive, from one or more sensors monitoring a set medical items stored in an inventory space of a medical facility, an indication of removal of one or more medical items of the set of medical items from the inventory space, generate, based on the received indication, a record of removal of the one or more medical items from the inventory space at the inventory management system, where the record specifies item usage information that is associated with an identity of a user that removed the one or more medical items, store, in association with the record of removal, an image of the user that removed the one or more medical items based on receiving the indication of the removal, the image being captured by the one or more sensors, and transmit, to a client application associated with the inventory management system, an indication of the record specifying the usage information and the identity of the user.

Some examples of the method, apparatuses, and non-transitory computer-readable medium described herein may further include operations, features, means, or instructions for monitoring, in response to receiving the indication the removal, a duration of item removal associated with the one or more medical items, determining that the duration of item removal exceeds a threshold time, and transmitting, to the client application associated with the inventory management system, an alert indicating that the duration of item removal exceeds the threshold time.

Some examples of the method, apparatuses, and non-transitory computer-readable medium described herein may further include operations, features, means, or instructions for determining that the identity of the user may be an unknown identity, and transmitting, to the client application, an alert indicating that the one or more medical items may have been removed by the user with the unknown identity, where the alert includes a link for accessing the image.

Some examples of the method, apparatuses, and non-transitory computer-readable medium described herein may further include operations, features, means, or instructions for transmitting, based on the user having the unknown identity, a bill for the one or more medical items that may be removed.

In some examples of the method, apparatuses, and non-transitory computer-readable medium described herein, the one or more sensors include at least one radio-frequency identifier (RFID) sensor and at least one camera, the at least on RFID sensor detecting an RFID tag corresponding to each of the one or more medical items, the at least one camera capturing the image of the user.

In some examples of the method, apparatuses, and non-transitory computer-readable medium described herein, generating the record of removal may include operations, features, means, or instructions for assigning the one or medical items to the user, where the user may be an authorized clinician.

Some examples of the method, apparatuses, and non-transitory computer-readable medium described herein may further include operations, features, means, or instructions for detecting, via the client application associated with the inventory management system, an access request to the record of the one or more medical items, the access request received from the authorized user, and transmitting, in response to the access request, an indication of information for a set of patients associated with the medical facility.

Some examples of the method, apparatuses, and non-transitory computer-readable medium described herein may further include operations, features, means, or instructions for accessing a patient database for the set of patients to retrieve the information for the set of patients.

Some examples of the method, apparatuses, and non-transitory computer-readable medium described herein may further include operations, features, means, or instructions for receiving, from the client application and from the user as an authorized user, an indication of an assignment of a medical item of the one or more medical items to a patient of the medical facility.

Some examples of the method, apparatuses, and non-transitory computer-readable medium described herein may further include operations, features, means, or instructions for generating, based on the indication of the assignment, one or more forms based on information associated with the patient, and transmitting, to the client application, an indication of the one or more forms.

Some examples of the method, apparatuses, and non-transitory computer-readable medium described herein may further include operations, features, means, or instructions for receiving, from the client application, an indication of acceptance of the one or more forms, a signature for the one or more forms, or a combination thereof.

Some examples of the method, apparatuses, and non-transitory computer-readable medium described herein may further include operations, features, means, or instructions for generating, based on receiving the indication of the assignment, a bill estimation using information association with the patient, and transmitting, to the client application, an indication of the bill estimation.

In some examples of the method, apparatuses, and non-transitory computer-readable medium described herein, generating the bill estimation may include operations, features, means, or instructions for retrieving insurance eligibility information based on insurance information associated with the patient.

Some examples of the method, apparatuses, and non-transitory computer-readable medium described herein may further include operations, features, means, or instructions for receiving, from the client application, payment information associated with payment of at least a copay associated with the assignment of the medical item to the patient.

Some examples of the method, apparatuses, and non-transitory computer-readable medium described herein may further include operations, features, means, or instructions for accessing a payment system to generate a payment form for the client application, where the payment information may be received in accordance with the payment form.

Some examples of the method, apparatuses, and non-transitory computer-readable medium described herein may further include operations, features, means, or instructions for updating inventory information for the assigned medical item associated with the inventory space, the medical facility, or both, based on receiving the indication of the assignment.

Some examples of the method, apparatuses, and non-transitory computer-readable medium described herein may further include operations, features, means, or instructions for generating a purchase order for one or more additional medial items of the assigned medical item based on updating the inventory information, and transmitting the order for the one or more additional medical items to a supplier associated with the assigned medical item.

In some examples of the method, apparatuses, and non-transitory computer-readable medium described herein, the order may be generated based on a minimum freight determination associated with the supplier.

In some examples of the method, apparatuses, and non-transitory computer-readable medium described herein, the minimum freight determination aggregates one or more other medical items associated with the supplier.

Some examples of the method, apparatuses, and non-transitory computer-readable medium described herein may further include operations, features, means, or instructions for transmitting, to the client application, an alert indication of a minimum freight determination, a deadline associated with the purchase order, or a combination thereof, where the purchase order may be generated based on the alert indication.

Some examples of the method, apparatuses, and non-transitory computer-readable medium described herein may further include operations, features, means, or instructions for receiving, from the one or more sensors, an indication of arrival of at least one of the one or more medical items, and updating the inventory based on the indication of the arrival.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a digital signal processor (DSP) and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable read only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein but is to be accorded the broadest scope consistent with the principles and novel features disclosed herein.

What is claimed is:

1. A method for data processing at an inventory management system, comprising:
   receiving, from a radio frequency identifier sensor that is configured to monitor a plurality medical items stored in an inventory space of a medical facility and prior to assignment of one or more medical items to a patient of the medical facility, an indication of removal of the one or more medical items of the plurality of medical items from the inventory space, wherein the inventory space is an open inventory space that is accessible without authenticating to the inventory space before entering;
   receiving, based at least in part on receiving the indication of removal from the radio frequency identifier sensor, an image of a user that removed the one or more medical items, the image being captured by at least one camera positioned at the inventory space;
   generating, based at least in part on the received indication, a record of removal of the one or more medical items from the inventory space at the inventory management system, wherein the record specifies item usage information that indicates assignment of the one or more medical items to an identity of the user that removed the one or more medical items, wherein the identity of the user is determined based at least in part on receiving the indication of removal of the one or more medical items;
   storing, in association with the record of removal, the image of the user that removed the one or more medical items based at least in part on receiving the indication of the removal;
   transmitting, to a client application associated with the inventory management system, an indication of the record specifying the item usage information and the identity of the user;
   receiving, via the client application, an indication of assignment of a medical item of the one or more medical items to a patient of the medical facility;
   generating, in response to receiving the indication of the assignment, billing information associated with assignment of the medical item to the patient, the billing information generated using information associated with the medical item and information associated with the patient that is retrieved from a patient database associated with the medical facility;
   transmitting, to the client application, the generated billing information associated with assignment of the medical item to the patient; and
   receiving, from the client application, in response to transmitting the billing information associated with assignment of the medical item to the patient, an indication of acceptance of the billing information by the patient.

2. The method of claim 1, further comprising:
   monitoring, in response to receiving the indication of the removal, a duration of item removal associated with the one or more medical items;
   determining that the duration of item removal exceeds a threshold time; and
   transmitting, to the client application associated with the inventory management system, an alert indicating that the duration of item removal exceeds the threshold time.

3. The method of claim 1, further comprising:
   receiving an indication of removal, by a second user, of a second medical item of the plurality of medical items from the inventory space;
   determining that an identity of the second user is an unknown identity; and
   transmitting, to the client application, an alert indicating that the second medical item has been removed by the second user with the unknown identity, wherein the alert includes a link for accessing an image of the second user.

4. The method of claim 3, further comprising:
   transmitting, to the medical facility and based at least in part on the second user having the unknown identity, a bill for the second medical item that is removed.

5. The method of claim 1, wherein generating the record of removal comprises:
   assigning the medical item to the user, wherein the user is an authorized clinician.

6. The method of claim 1, further comprising:
   detecting, via the client application associated with the inventory management system, an access request to the record of the one or more medical items, the access request received from the user that is an authorized user; and
   transmitting, in response to the access request, an indication of information for a plurality of patients associated with the medical facility.

7. The method of claim 6, further comprising:
   accessing a patient database for the plurality of patients to retrieve the information for the plurality of patients.

8. The method of claim 1, further comprising:
   generating, based at least in part on the indication of the assignment, one or more forms based at least in part on information associated with the patient; and
   transmitting, to the client application, an indication of the one or more forms.

9. The method of claim 1, wherein generating the billing information comprises:
   transmitting, to an insurance application, patient eligibility data that includes an indication of the information associated with the patient and an indication of the medical item; and
   receiving, in response to transmitting the patient eligibility data and from the insurance application, the billing information including a bill estimation, wherein the billing information is transmitted to the client application in response to receiving the billing information.

10. The method of claim 9, wherein the received billing information comprises deductibles, remaining deductibles, co-pays, co-insurance, out of pocket amounts, exclusions, limitations, or a combination thereof.

11. The method of claim 1, wherein receiving the indication of acceptance of the billing information by the patient comprises:
    receiving, from the client application in response to transmitting the generated billing information associated with assignment of the medical item to the patient, payment information associated with payment of at least a copay associated with the assignment of the medical item to the patient.

12. The method of claim 1, further comprising:
updating inventory information for the assigned medical item associated with the inventory space, the medical facility, or both, based at least in part on receiving the indication of the assignment.

13. The method of claim 12, further comprising:
generating a purchase order for one or more additional medial items corresponding to the assigned medical item based at least in part on updating the inventory information; and
transmitting the purchase order for the one or more additional medical items to a supplier associated with the assigned medical item.

14. The method of claim 13, wherein the purchase order is generated based at least in part on a minimum freight determination associated with the supplier.

15. The method of claim 14, wherein the minimum freight determination aggregates one or more other medical items associated with the supplier.

16. The method of claim 13, further comprising:
transmitting, to the client application, an alert indication of a minimum freight determination, a deadline associated with the purchase order, or a combination thereof, wherein the purchase order is generated based at least in part on the alert indication.

17. An apparatus for data processing at an inventory management system, comprising:
a processor, memory coupled with the processor; and
instructions stored in the memory and executable by the processor to cause the apparatus to:
receive, from a radio frequency identifier sensor that is configured to monitor a plurality medical items stored in an inventory space of a medical facility and prior to assignment of one or more medical items to a patient of the medical facility, an indication of removal of the one or more medical items of the plurality of medical items from the inventory space, wherein the inventory space is an open inventory space that is accessible without authenticating to the inventory space before entering;
receive, based at least in part on receiving the indication of removal from the radio frequency identifier sensor, an image of a user that removed the one or more medical items, the image being captured by at least one camera positioned at the inventory space;
generate, based at least in part on the received indication, a record of removal of the one or more medical items from the inventory space at the inventory management system, wherein the record specifies item usage information that indicates assignment of the one or more medical items to an identity of the user that removed the one or more medical items, wherein the identity of the user is determined based at least in part on receiving the indication of removal of the one or more medical items;
store, in association with the record of removal, the image of the user that removed the one or more medical items based at least in part on receiving the indication of the removal;
transmit, to a client application associated with the inventory management system, an indication of the record specifying the item usage information and the identity of the user receive, via the client application, an indication of assignment of a medical item of the one or more medical items to a patient of the medical facility;
generate, in response to receiving the indication of the assignment, billing information associated with assignment of the medical item to the patient, the billing information generated using information associated with the medical item and information associated with the patient that is retrieved from a patient database associated with the medical facility;
transmit, to the client application, the generated billing information associated with assignment of the medical item to the patient; and
receive, from the client application, in response to transmitting the billing information associated with assignment of the medical item to the patient, an indication of acceptance of the billing information by the patient.

18. A non-transitory computer-readable medium storing code for data processing at an inventory management system, the code comprising instructions executable by a processor to:
receive, from a radio frequency identifier sensor that is configured to monitor a plurality medical items stored in an inventory space of a medical facility and prior to assignment of one or more medical items to a patient of the medical facility, an indication of removal of the one or more medical items of the plurality of medical items from the inventory space, wherein the inventory space is an open inventory space that is accessible without authenticating to the inventory space before entering;
receive, based at least in part on receiving the indication of removal from the radio frequency identifier sensor, an image of a user that removed the one or more medical items, the image being captured by at least one camera positioned at the inventory space;
generate, based at least in part on the received indication, a record of removal of the one or more medical items from the inventory space at the inventory management system, wherein the record specifies item usage information that indicates assignment of the one or more medical items to an identity of the user that removed the one or more medical items, wherein the identity of the user is determined based at least in part on receiving the indication of removal of the one or more medical items;
store, in association with the record of removal, the image of the user that removed the one or more medical items based at least in part on receiving the indication of the removal;
transmit, to a client application associated with the inventory management system, an indication of the record specifying the item usage information and the identity of the user;
receive, via the client application, an indication of assignment of a medical item of the one or more medical items to a patient of the medical facility;
generate, in response to receiving the indication of the assignment, billing information associated with assignment of the medical item to the patient, the billing information generated using information associated with the medical item and information associated with the patient that is retrieved from a patient database associated with the medical facility;
transmit, to the client application, the generated billing information associated with assignment of the medical item to the patient; and
receive, from the client application, in response to transmitting the billing information associated with assignment of the medical item to the patient, an indication of acceptance of the billing information by the patient.

* * * * *